United States Patent [19]

Scheinberg

[11] Patent Number: 5,730,982
[45] Date of Patent: Mar. 24, 1998

[54] THERAPEUTIC USE OF HYPERVARIABLE REGION OF MONOCLONAL ANTIBODY M195 AND CONSTRUCTS THEREOF

[75] Inventor: David A. Scheinberg, New York, N.Y.

[73] Assignee: Sloan-Kettering Institute for Cancer Research, New York, N.Y.

[21] Appl. No.: 383,615

[22] Filed: Feb. 2, 1995

Related U.S. Application Data

[63] Continuation of Ser. No. 56,957, May 3, 1993, abandoned, which is a continuation of Ser. No. 450,918, Dec. 14, 1989, abandoned.

[51] Int. Cl.[6] .................. A61K 39/395; C07K 16/28
[52] U.S. Cl. .................. 424/181.1; 424/183.1; 530/388.22; 530/391.3; 530/391.5; 530/391.7; 530/391.9
[58] Field of Search .............. 530/391.3, 391.7, 530/387.7, 388.7, 387.3, 388.22, 391.5, 391.9; 435/240.27; 424/178.1, 183.1, 144.1, 154.1, 155.1, 181.1

[56] References Cited

PUBLICATIONS

Scheinberg et al. Leukemia 3:440–445, 1989.
Tanimoto et al. Leukemia 3:339–348, 1989.
Andrews et al. Blood 62:124–132, 1983.
Bernstein et al. J. Clin Invest. 79:1153–1159, 1987.
Shawler et al. Cancer Res. 44:5921–5927, 1984.
Peiper et al. pp. 622–625 in Leulcocyte Typing III, MaeMichael et al. Ed. Oxford Univ. Press 1986.
Houghton et al. Seminars in Clinical Oncology 13: 165–179 1986.
Morrison Science 229:1202–1207, 1983.
Waldman Science 252:1657–1662, 1991.
Blakey et al., "Monoclonal Antibody Therapy Prog Allergy", H. Waldmann Ed., Basel Karger 1988, vol. 45. pp. 50–90.
Engleman et al., Eds. "Human Hybridomas and Monoclonal Antibodies", Plenum Press, 1985, pp. 160–161.

*Primary Examiner*—Lila Feisee
*Assistant Examiner*—Nancy A. Johnson
*Attorney, Agent, or Firm*—John P. White

[57] ABSTRACT

Therapeutic agents and methods for treating and diagnosing acute or chronic leukemia are provided. Such agents comprises monoclonal antibody M195, or a chimeric antibody containing the hypervariable region of M195, conjugated to a cytotoxic agent, e.g. a radioisotope.

21 Claims, 17 Drawing Sheets

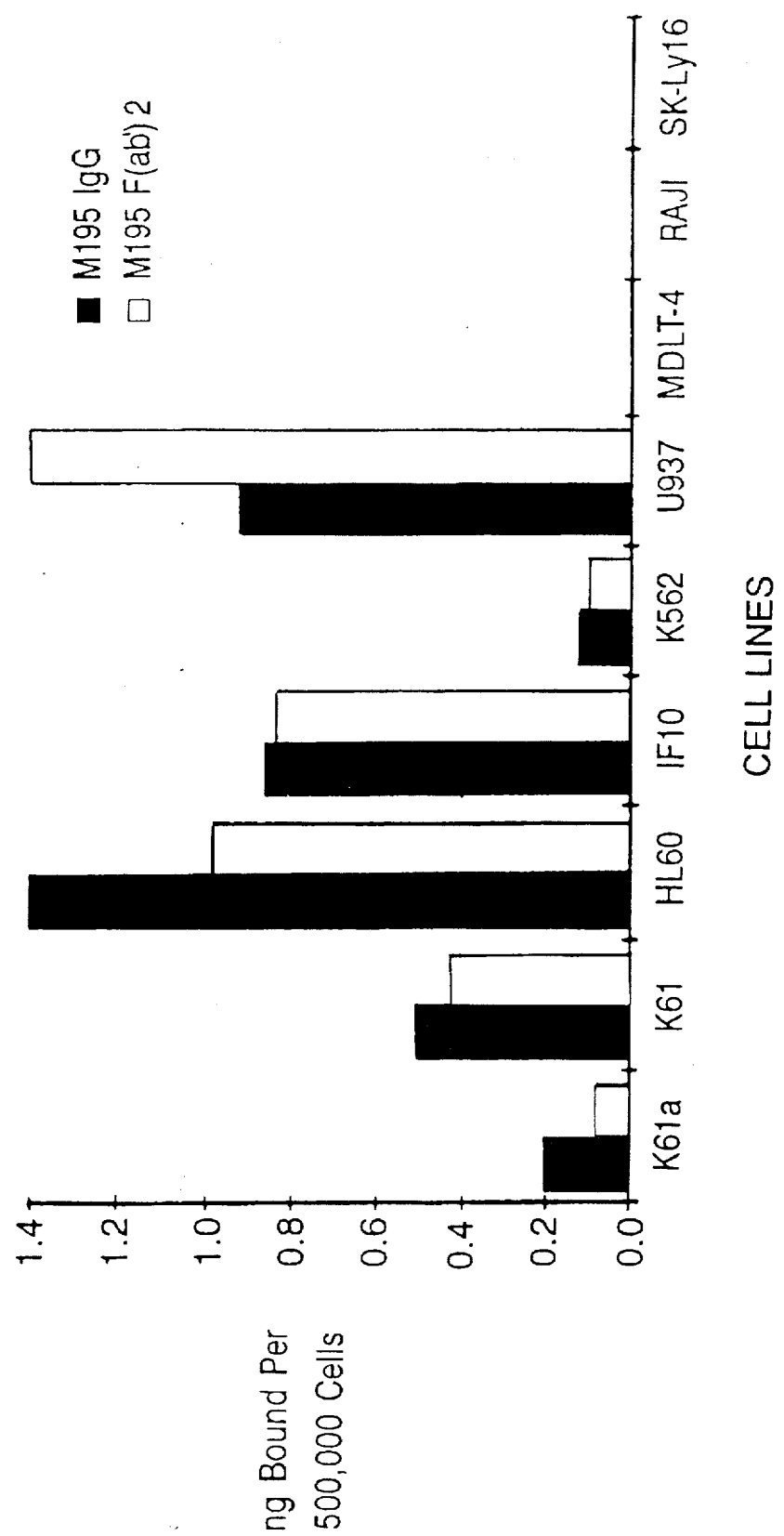

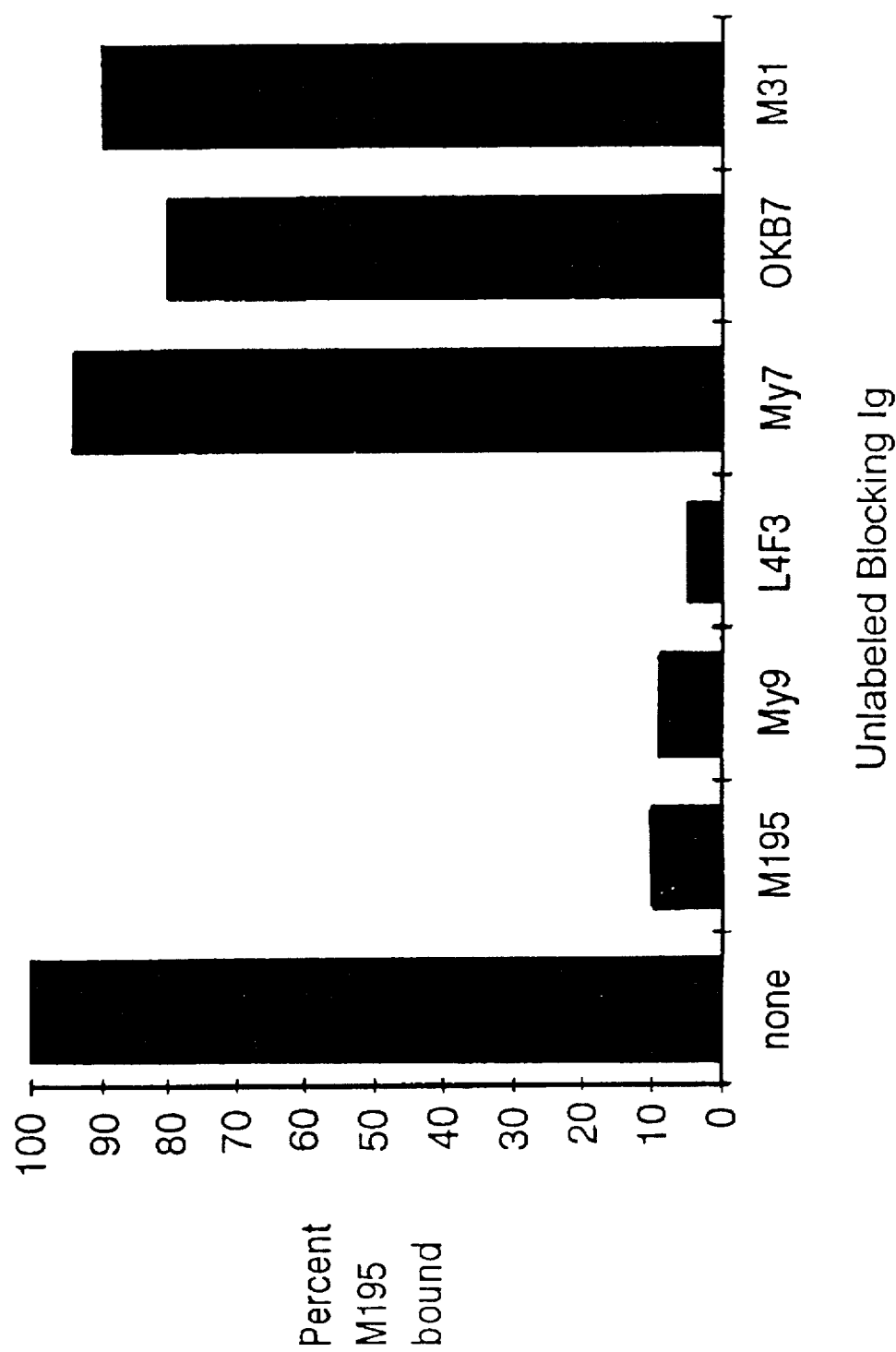

In-111 M195 Internalization

Expression of The M195 Antigen

FIG. 13
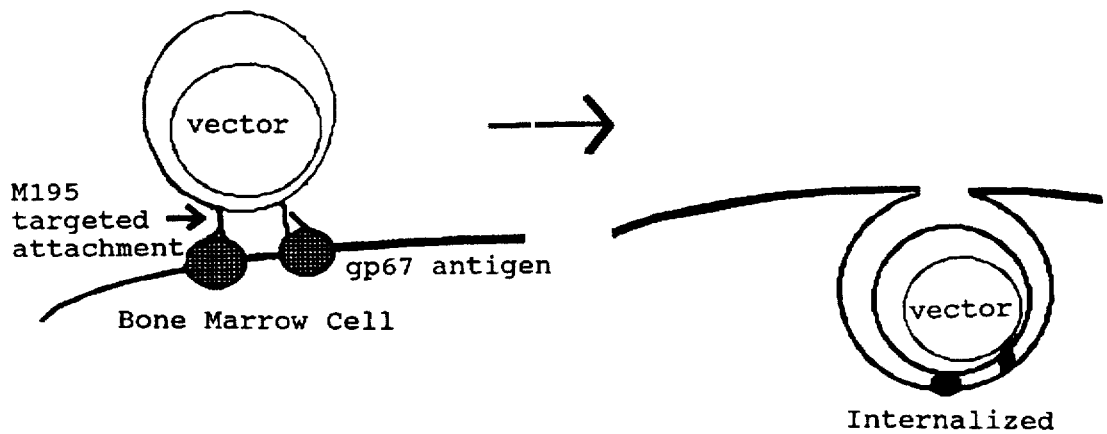
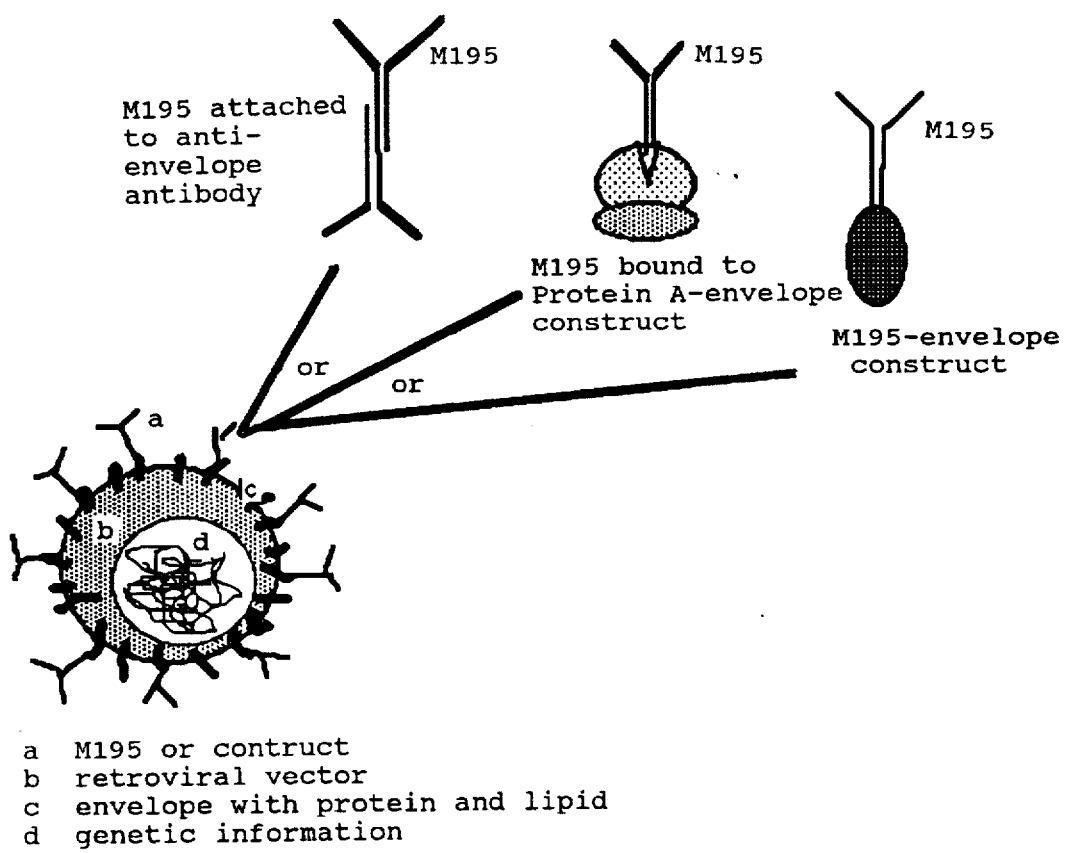
a  M195 or contruct
b  retroviral vector
c  envelope with protein and lipid
d  genetic information

THERAPEUTIC USE OF HYPERVARIABLE REGION OF MONOCLONAL ANTIBODY M195 AND CONSTRUCTS THEREOF

This is a continuation of U.S. application Ser. No. 08/056,957, filed May 3, 1993, which is a continuation of U.S. Ser. No. 07/450,918, filed Dec. 14, 1989, now abandoned, the contents of which are hereby incorporated by reference.

The invention disclosed herein was made with Government support under NIH Grant No. CA08748 from the Department of Health and Human Services. Accordingly, the U.S. Government has certain rights in this invention.

Throughout this application, various publications are referenced by numbers within parentheses. Full citations for these publications may be found at the end of the specification immediately preceding the claims. The disclosure of these publications, in their entireties, are hereby incorporated by reference into this application in order to more fully describe the state of the art to which this invention pertains.

BACKGROUND OF THE INVENTION

Mouse monoclonal antibody M195 is an IgG2a developed at Sloan-Kettering Institute (Tanimoto M., Scheinberg D A, Cordon-Cardo C, et al. Leukemia 3:339–348, 1989. Scheinberg D A, Tanimoto M, McKenzie S, et al. Leukemia 3:440–445, 1989.) which reacts with 60–70% of samples of blasts from patients with ANLL. M195 also binds to early myeloid cells (CFU-GM) and some monocytes but not to the earliest myeloid progenitors. The target antigen is not expressed on any other hematopoietic or non-hematopoietic tissue. Antibodies to a related antigen on the same protein (CD33), My9 and L4F3, are currently being used to purge bone marrow of ANLL before autologous transfusion (Bernstein I D, Singer J W, Andrews R G, et al. J Clin Invest 79:1153–1159, (1987); Griffin J D, Linch D, Sabbath K, et al. Leukemia Res 8:521–534, 1984.). M195 is rapidly internalized into cells after binding and this effect can enhance delivery of radiometals, radioiodine or conjugated toxins into cells (Divgi C R, Minniti J G, Old L J, Scheinberg D A Amer Assoc Cancer Res 30: Abs #1606, 1989). M195 is able to kill leukemia cells with rabbit or guinea pig complement, but not by use of human complement or human antibody-dependent cellular cytotoxicity in vitro. Activation of these mediators in vitro has correlated with these effects in vivo (Houghton A N, Mintzer D, Cordon-Cardo C, et al. Proc Natl Acad Sci USA 82:1242–1246, (1985)), but it is not known if the lack of in vitro effects will predict lack of in vivo effects. Because M195 also reacts with early myeloid cells, normal marrow progenitors may be affected also.

Long-term survival in ANLL with the best current chemotherapeutic regimens is generally less than 20% (Clarkson B D, Gee T S, Mertelsmann R, et al. CRC critical review in Oncology/Hematology 4:221–248 (1986)). Survival of patients who relapse or who fail first attempts at induction chemotherapy is far lower. Autologous or allogeneic bone marrow transplantation may improve survival, but only in a small subset of patients (Gale R P, Horowitz M M, Biggs J C, et al. Lancet 8647:1119–1121 (1989)). There are no effective therapies for myelodysplastic syndromes or chronic monocytic leukemias and long term survival in these diseases is rare. Among patients with chronic myeloid leukemias (CML), only allogeneic bone marrow transplant has had an impact on survival (Clarkson B D J Clin Oncol 3:135–139 (1985)).

(Ref.a "Mab195: A Diagnostic Marker . . . "): Monoclonal antibodies (mAb) reactive with differentiation antigens present on myeloid cells and their progenitors are being used to study hematopoietic differentiation, to identify acute nonlymphoid leukemia (ANLL), to study the effects of hematopoietic growth factors, to purge bone marrow of leukemia cells, and for therapy in vivo (1–15 Ref.a).

(Ref.b "Restricted Antigens . . . "): The antigens displayed on the surface of acute non-lymphocytic leukemia (ANLL) cells and hematopoietic progenitor cells are being mapped in a number of laboratories using monoclonal antibodies (mAbs) (1 Ref.b). These studies have been directed at identifying antigens that are useful in distinguishing lymphoid from nonlymphoid leukemias (2–4 Ref.b), in subtyping of acute myelogenous leukemia, and in predicting outcome (5–10 Ref.b) and in therapy in vivo (11 Ref.b) or via bone marrow purging ex vivo (12 Ref.b). Antigens defining ANLL cells also identify normal hematopoietic cells during early stages of their development and thus should be classified as differentiation antigens rather than leukemia specific antigens.

Antigens restricted to the earliest stages of hematopoietic development are of particular interest since ANLL is thought to be derived from these cells (13–16 Ref.b). mAbs identifying these early cells can help in their purification or the study of growth regulation and control of differentiation (17 Ref.b). Such early progenitors may be useful for autologous reinfusion in bone marrow rescue (18 Ref.b). Studies of bone marrow from patients with ANLL have shown that the clonogenic cells are probably derived from a subset of cells which are phenotypically more immature that the majority of cells in circulation (14, 15 Ref.b). This suggests that analysis of the development of leukemia cells, as well as therapeutic trials, should also be directed at these early cells and not simply the phenotypically predominant cells in the marrow and peripheral blood.

Several mAbs restricted to hematopoietic progenitors have been described: monoclonal antibodies MY10, 3C5, and 12.8 recognize a 115-kDa glycoprotein (gp115 [CD34]) found on normal colony forming cells, myeloblasts, and leukemic blasts from most patients with ANLL and acute lymphoid leukemias (19–21 Ref.b). mAb NHL-30.5 identifies a 180-kDa protein found on a similar distribution of cells (22, 23 Ref.b). My9 and L4F3 antibodies identify a 67-kDa glycoprotein (CD33) (24–27 Ref.b) which is expressed on slightly more mature progenitors (subsets of CFU-GEMM and some older cells) and is restricted to leukemias of the myeloid and monocytic lineage. Long-term culture studies suggest that elimination of cells bearing the CD33 antigen will still allow regrowth of normal marrow cells of all lineages, presumably because of the presence of more immature antigen negative progenitors (25 Ref.b). Sabbath et al. (15 Ref.b) show that the CD33 antigen is expressed on leukemic colony-forming cells whereas other more mature markers are less commonly expressed. Finally, studies with ANLL marrow suggest it may be possible to purge leukemia cells from the bone marrow of many patients with ANLL using complement fixing antibodies to CD33 without destroying the ultimate normal progenitors (24 Ref.b). Several other antibodies with a less restricted distribution have also been described (14, 28, 29 Ref.b).

(Ref.c): Since the discovery of hybridoma technology by Kohler and Milstein (1Ref. c), there has been considerable interest in the utility of monoclonal antibodies as carriers of radioactivity for the diagnosis and therapy of cancer (2,3Ref. c). After the initial report by Goldenberg et al. on the utility of radiolabeled antibodies in the detection of cancer (4), there have been several clinical trials utilizing radiolabeled monoclonal antibodies in lymphoma and leukemia (5–11

Ref.c), both for radioimmunolocalization and radioimmunotherapy. Most of these trials have employed radioiodine (5–10 Ref.c); Carrasquillo and associates have also studied $^{111}$In-labeled monoclonal antibody T101 (5,9 Ref.c) in the diagnosis of T-cell lymphoma. One obvious advantage of radiolabeled antibodies is that the specificity of antibody for the target antigen, often expressed in increased quantities on neoplastic cells, offers a potentially useful method for the selective delivery of radioactivity to the tumor site; moreover, the range of potentially lethal radiation emitted by most currently used radionuclides extends over several cell diameters, making it theoretically possible for the radiation to be cytotoxic to neighboring neoplastic cells that lack the target antigen.

Historically, beta-minus particle emitters such as $^{131}$I have been preferred for mAb directed radioimmunotherapy. Radionuclides such as $^{125}$I that decay by electron capture are also of interest in radioimmunotherapy because they are cytotoxic when internalized by the cell nucleus (12 Ref.c). $^{125}$I labeled antibodies that are internalized into the cell following interaction with the target antigen may thus be cytotoxic (13 Ref.c). Studies in both animals and humans have shown that the radiometal $^{111}$In concentrates to a significantly greater extent in tumor compared to radioiodine (14–17 Ref.c). Thus, use of beta-minus emitting radiometals such as $^{90}$Y are of interest for therapy as well. Therefore, the choice of radionuclide used to label monoclonal antibodies may be of importance in the design of clinical trials utilizing radiolabeled mAbs for diagnosis and therapy.

Antigen-antibody complexes may either be shed from the cell or internalized into the cell following interaction with antibody. This process, known as modulation, was first described in mice (18 Ref.c) and later confirmed to occur during trials of mAb in humans (19 Ref.c). The process appears to be a general phenomenon found in many antigen-antibody systems of hematopoietic cells (20 Ref.c) and neoplasms as well as in solid tumors (21 Ref.c). Modulation may result in mAb shedding, internalization, or both processes. Shedding may result in residence time of the antibody on the target cell too short to achieve cell kill. On the other hand, internalized antigen-antibody complexes may theoretically deliver significant amounts of cytotoxic antibody into the cell if the cytotoxic label attached to the antibody is internalized into the cell and retained.

The cell biology of modulation and receptor internalization has been studied elsewhere (22,23 Ref.c).

SUMMARY OF THE INVENTION

This invention provides a recombinant polypeptide which comprises an amino acid sequence which is substantially the same as the amino acid sequence of the hypervariable region of monoclonal antibody M195 (ATCC No. HB 10306).

The invention further provides a chimeric antibody which comprises such a polypeptide, particularly in combination with the amino acid sequences of a human framework region and of a constant region from a human antibody.

Still further, this invention provides a therapeutic agent comprising such a chimeric antibody and a cytotoxic agent for example, a radioisotope or a toxin conjugated thereto. Also, this invention provides a therapeutic agent comprising monoclonal antibody M195 (ATCC No. HB 10306) and a cytotoxic agent conjugated thereto.

This invention additionally provides methods of treating or diagnosing acute or chronic leukemia in human patients, of effecting bone marrow transplants, and introducing genetic information into leukemia cells.

BRIEF DESCRIPTION OF THE FIGURES

FIG. 1A, Total (◊), nonspecific (binding of $^{125}$I-IgG in the presence of excess unlabeled IgG (♦), and specific (■) binding of M195 IgG to HL60 leukemia cells. FIG. 1B, Scatchard plot of M195 IgG binding. FIG. 1C, Scatchard plot of M195 F(Ab)'2 binding.

FIG. 2. Radioimmunoassay of M195 IgG and F(Ab)'2 on cell lines of hematopoietic origin. $^{125}$I-M195 binding was determined at saturation as described in Materials and Methods. Nonspecific binding was 0.2 ng 500,000 cells. Only specific binding is shown: IgG, ■; F(Ab)'2,■

FIG. 4A, photomicrograph of M195 IgG binding to trophoblast. FIG. 4B, Control IgG binding to trophoblast cells.

FIG. 7. Blocking of M195 direct radioimmunoassay by excess unlabeled Ig. A 50–100 fold molar excess of the antibodies designated along the X axis were added to HL60 target cells followed by $^{125}$I-M195 at 4° C. for 60 min. The amount of bound $^{125}$I-M195 is shown on the Y axis. Binding of M195 without competing IG was normalized to 100%

Figure 8A:
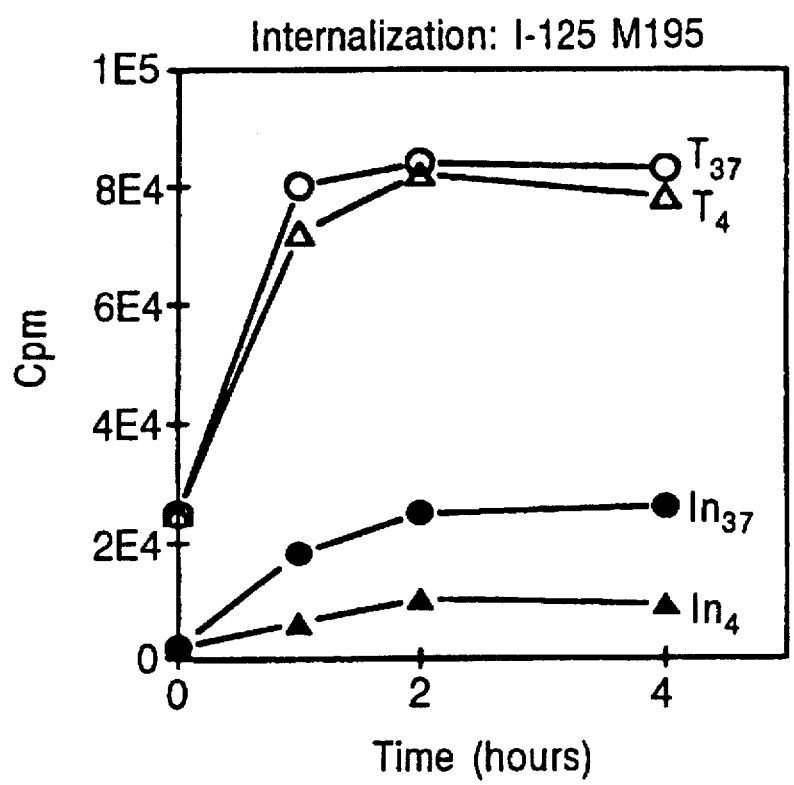
FIG. 8A–8D. $^{125}$I-M195 Internalization & Release.

Internalization (FIGS. 8A, 8B): 5 million HL60 cells were mixed with 5 μg mAb or fragment and incubated at 4° or 37°. Aliquots were taken at appropriate time points and measured for total and internalized cell-associated radioactivity.

All graphs showing radioactivity in counts per minute over time are labeled as follows: (△—△): total cell-associated radioactivity at 4° C.; (○—○): total cell-associated radioactivity at 37° C.; (▲—▲): internalized radioactivity at 4° C.; (●—●) internalized radioactivity at 37° C.

All graphs showing percent internalized radioactivity are labeled as follows (▲—▲): percent internalized at 4° C.; (○—○); percent internalized radioactivity at 37° C.

Release (FIGS. 8C, 8D): 5 million cells were incubated with 5 μg mAb or fragment at 4° for 60 minutes, then washed free of ambient mAb. Measurements of internalized radioactivity were carried out as described above with the washed cells being kept at 4° or 37°. The symbols for these graphs are as for internalization data.

FIGS. 9A–9D. $^{111}$In-M195 Internalization & Release.

Internalization (FIGS. 9A, 9B): Conducted exactly as described in FIGS. 8A, 8B except M195 is now labeled with In-111.

Release (FIGS. 9A, 9B): Conducted exactly as described in FIGS. 8C, 8D except M195 is now labeled in this experiment with In-111.

FIGS. 10A–10D. $^{125}$I-M195 F(ab')2 Internalization & Release.

Internalization (FIGS. 10A, 10B): Conducted exactly as described in FIGS. 8A, 8B except I-$^{125}$ is now attached to F(ab')$_2$ fragment of M195.

Release (FIGS. 10C, 10D): Conducted as described in FIGS. 8c, 8d except M195 F(ab')$_2$ is now labeled with I-125.

Figure 11:
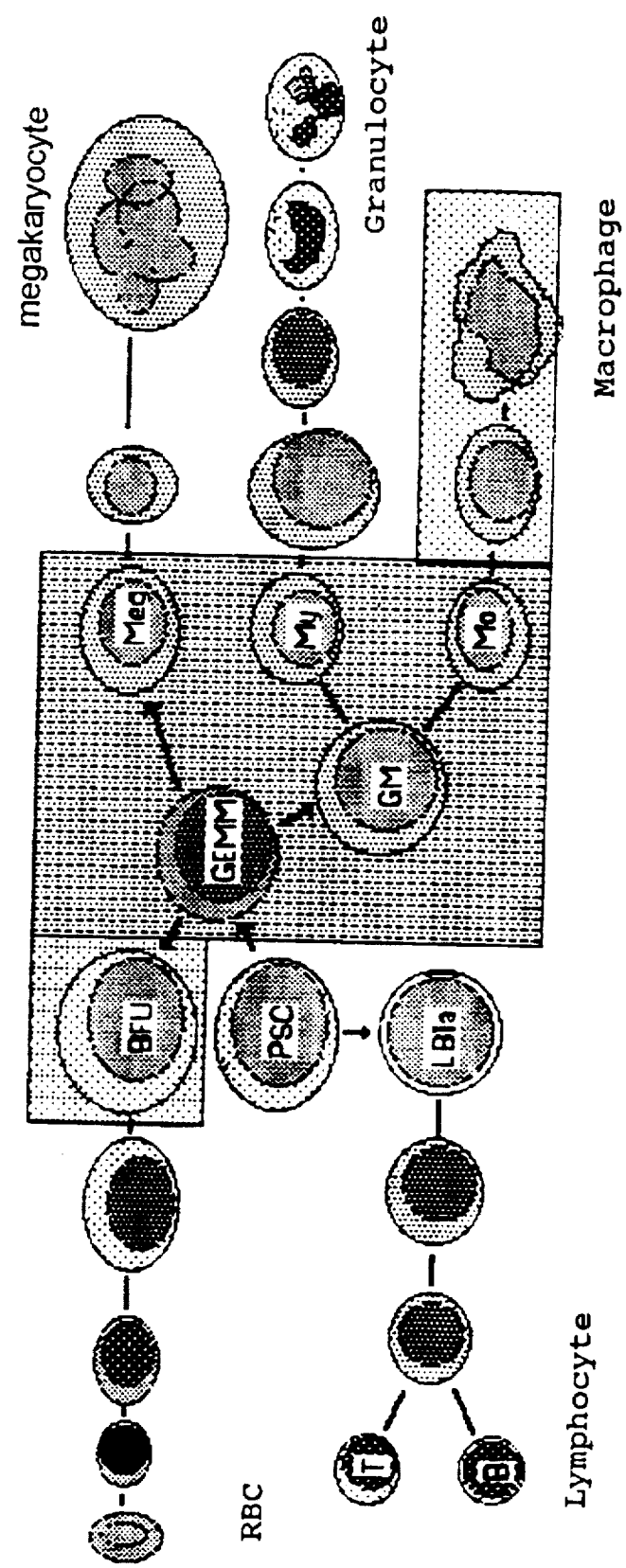

FIG. 11. Schematic diagram of the distribution of the M195 antigen in human tissues. The antigen is not known to be present on any adult non-hematopoietic tissues, so they are not shown. The distribution in the hematopoietic cells is shown.

Figure 12:

FIG. 12. Posterior and anterior whole body gamma camera images of patient #1, injected 18 hours earlier with 5 mCi iodine-131 M195 (1.5 mg). All known areas of leukemic involvement (bone marrow, spleen, liver, mediastinal chlorama) show marked uptake of M195.

FIG. 13. Schematic diagram of the method of antibody targeting of genetic information into hematopoietic cells

DETAILED DESCRIPTION OF THE INVENTION

The invention provides a recombinant polypeptide which comprises an amino acid sequence which is substantially the same as the amino acid sequence of the hypervariable region of monoclonal antibody M195 (ATCC No. HB 10306).

The hybridoma which produces the monoclonal antibody designated M195 has been deposited with the American Type Culture Collection in Rockville, Md., U.S.A. 20852, under ATCC Accession No. HB 10306 on Dec. 14, 1989. This deposit was made pursuant to the provisions of the Budapest Treaty on the International Recognition of the Deposit of Microorganisms for the Purposes of Patent Procedure (Budapest Treaty).

Also, one may obtain such a polypeptide by nonrecombinant methods, such as for example, proteolytic digestion.

A chimeric antibody comprising such a recombinant polypeptide is also provided, particularly a chimetic antibody comprising the amino acid sequences of a human framework region and of a constant region from a human antibody so as to "humanize" or render nonimmunogenic the hypervariable region of the mouse M195 monoclonal antibody.

This invention also concerns a therapeutic agent comprising such a chimeric antibody and a cytotoxic agent conjugated thereto.

Of particular interest are therapeutic agents wherein the cytotoxic agent is a radioisotope, such as an alpha particle emitter, for example one selected from the group consisting of Lead-212, Bismuth-212, and Astatine-212

In one embodiment of the therapeutic agent, the alpha particle emitter is conjugated to the chimeric antibody by means of a bifunctional chelate.

Alternatively, the cytotoxic agent present in the therapeutic agent may be a beta particle emitter, e.g. one selected from the group consisting of Iodine-131, Scandium-47, Rhenium-186, Rhenium-188, and Yttrium-90.

Still further, the radioisotope may be an auger electron generator, e.g. one selected from the group consisting of Iodine-123, Iodine-125, Bromine-77, and Indium-111. or a fissionable nuclide such as Boron-10 or an Actinide.

A therapeutic agent comprising monoclonal antibody M195 (ATCC HB 10306) and a cytotoxic agent conjugated thereto is also provided by this invention, e.g. one in which the cytotoxic agent is a radioisotope.

Also, this invention concerns a polypeptide comprising the recombinant polypeptide described hereinabove fused to another polypeptide, for example, a toxin or a drug.

This invention also provides a method of treating acute or chronic leukemia in a human patient which comprises administering to the patient an amount of the therapeutic agent comprising a chimeric antibody to which a cytotoxic agent is conjugated, sufficient to bind to, and be internalized by, leukemic cells so as to thereby destroy the leukemic cells.

Further, the invention concerns a method of treating acute or chronic leukemia in a human patient which comprises administering to the patient an amount of a therapeutic agent comprising M195 conjugated to a radioisotope sufficient to bind to, and be internalized by leukemic cells so as to thereby destroy the leukemic cells.

In such methods the amount of therapeutic agent is typically from about 0.05 mg. to about 100 mg and the therapeutic agent is administered intravenously.

Still further, this invention provides a method of treating acute or chronic leukemia in a human patient which comprises administering to the patient an amount of a therapeutic agent as described hereinabove sufficient to bind to, and be internalized by, leukemic cells so as to thereby destroy the leukemic cells.

In one embodiment, the therapeutic agent comprises Iodine-131 and the sufficient amount comprises from about 50 mCi to about 200 mCi. In another embodiment, the therapeutic agent comprises Yttrium -90 and the sufficient amount comprises from about 10 mCi to about 50 mCi. In yet another embodiment, the therapeutic agent comprises Bismut-212 and the sufficeint amount comprises from about 20 mC1 to about 80 mCi. In still another embodiment, the therapeutic agent comprises Iodine-123 and the sufficient amount comprises from about 100 mCi to about 300 mCi.

This invention additionally provides a method destroying a human patient's natural bone marrow cells which comprises administering to the patient an amount of the therapeutic agent according to the invention sufficient to destroy the patient's bone marrow cells under conditions such that the therapeutic agent binds to, is internalized by, and destroys the bone marrow cells.

Thus, the therapeutic agent may comprise monoclonal antibody M195 (ATCC Accession No. HB 10306) and a cytotoxic agent conjugated thereto, the amount of antibody may be from about 0.01 mg. to about 50 mg; and the therapeutic agent may be administered intravenously.

Additionally, this invention concerns a method of treating leukemia which comprises removing bone marrow cells, including leukemia cells, from a human leukemic patient; contacting the bone marrow cells so removed with a sufficient amount of the therapeutic agent of the invention to bind to, be internalized by, and thereby destroy the leukemia cells present in the bone marrow cells; and autologously reinfusing the resulting bone marrow cells into the patient. Preferably, the contacting of the bone marrow cells, including leukemia cells, removed from the patient is effected in the presence of rabbit or guinea pig complement.

Additionally, this invention concerns a method of diagnosing acute or chronic leukemia in a human patient which comprises administering to the patient an antibody according to this invention labelled with an imaging agent under conditions so as to form a complex between the antibody and any leukemia cells present in the patient, imaging any complex so formed, and thereby diagnosing acute or chronic leukemia Preferably, the imaging agent is internalized into the leukemia cells.

In one embodiment, the antibody is monoclonal antibody M195 (ATCC Accession No. HB 10306) and the imaging agent is a radioisotope such as a positron-emitting radiometal; a gamma-emmitting radiometal; Iodine-131; Iodine-123; Indium-111 or Technetium-99m.

Finally, this invention provides a method of introducing or carrying genetic information into leukemia cells which comprises contacting cells with the antibody of this invention to which the genetic information is attached or with which it is associated, so that the antibody binds to the cells to form a complex, which is thereafter internalized into the cells. so as to thereby introduce or carry the genetic information into the cells.

In one embodiment, the genetic information is in a retroviral vector attached to the antibody.

EXPERIMENT 1

This experiment and in experiment 2 describes a mouse monoclonal antibody, M195, which defines an antigen restricted to early myeloid cells, monocytic cells, and ANLL. The antigen appears to be carried on the CD33 protein. The antigen is not detectable on any other adult tissues and thus may be useful in the study of myelomonocytic differentiation and in the diagnosis and therapy of ANLL. This experiment describes the distribution of the antigen on cell lines, normal tissues, and mature hematopoietic cells. The antibody's biological activity, affinity, and quantitative distribution on individual cells are presented.

MATERIALS AND METHODS mAbs. mAb M195 was produced from hybridomas resulting from a fusion of SP2/0-Ag14 mouse myeloma cells and the spleen cells of a 5-week-old BALB/c mouse immunized with leukemia cells from a patient with ANLL (FAB-M2). Supernatant fluids from cloned hybridoma cultures were screened against a panel of leukemia cell lines and the original ANLL leukemia cells using *Staphylococcus aureus* protein A (PA) erythrocyte rosetting (see below). The repeatedly sub-cloned M195 hybridoma was expanded in the peritoneal cavity of doubly pristane-primed (C57BL/6× BALB/c) F1 mice.

M195 was purified on PA-Sepharose (Pharmacia) by affinity chromatography using sequential pH step elutions. Purity was determined on sodium dodecyl sulfate (SDS)-polyacrylamide gels stained with Coomassie brilliant blue.

Control antibodies included mAb AJ2, reactive with a broadly expressed cell surface antigen (VLA) produced at Sloan-Kettering (31 Ref.b), and mAb M31 (reactive with the Lewis X antigen) developed in this laboratory (unpublished).

Screening of Hybridoma Supernatants. Four thousand cells (HL60) or the original immunizing ANLL cells) in 10 µl of RPMI with 10% fetal calf serum (FCS) were allowed to settle and attach to concanavalin A-coated (Pharmacia) Terasaki 60-well plates (NUNC) for 45 min at 20° C. as described (32, 33 Ref.b). Hybridoma supernatants were tested for reactivity on these cells using PA-coated human O⁻ red blood cell rosettes as indicators (32 Ref.b).

Cells and Cell Lines. Heparinized peripheral blood samples and bone marrow aspirates were obtained from healthy volunteers and patients on the Leukemia Service at Memorial Hospital after informed consent. Mononuclear cells were separated on Ficoll-Paque (Pharmacia), and adherent cells were isolated from the nonadherent mononuclear cells by plastic adherence for 2 hr. at 37° C. Polymorphonuclear leukocytes were purified from contaminative red blood cells after dextran sedimentation at 1×g for 60 min by ammonium chloride lysis in Tris buffer at pH 7.2. Platelets were separated from the Ficoll-Paque interface cells by differential centrifugation. E-rosette-positive and negative fractions of mononuclear cells were separated after incubation and neuraminidase- (Calbiochem) treated sheep red blood cells (GIBCO), followed by Ficoll-Paque gradient centrifugation and lysis of red cells with ammonium chloride.

Hematopoietic cell lines (Table 1) and nonhematopoietic cell lines (Table 3) were obtained from the human tumor banks of the Human Cancer Immunology Laboratory at Sloan-Kettering Institute. 1F10 and 1F10 (mono), an HL60 subclone and its monocytic differentiated form, were the gift of Dr. Y. Cayre, Sloan-Kettering Institute (34 Ref.b).

Serologic Assays: Immune Rosetting. Antibody specificity was determined on adherent cell lines plated in 60 well Terasaki plates using Staphylococcus aureus PA or rabbit antimouse Ig-coated human O red blood cells prepared as described (32 Ref.b) as indicators. Suspension target cells are assayed using the same indicator cells except that the target cells were attached to Terasaki plates immediately before testing using Concanavalin A (33 Ref.b). This assay is sensitive to concentrations of mAb M195 of about 1 ng/ml binding to HL60. Cells were considered negative if no rosettes formed below an ascites dilution of 200 and absorption analyses were also negative. Ascites fluids were considered "weakly positive" on a cell line if greater than 50% of cells formed rosettes at dilutions between 200 and 100,000. "Weakly positive" cells were confirmed as reactive by absorption analysis (see below). Ascites from mice bearing hybridomas were considered positive with a cell line if rosetting of cells occurred at a dilution of greater than 100,000. If purified antibody was used, cell lines were scored "positive" for rosetting at concentrations below 50 ng/ml and "weakly positive" at concentrations of 50–500 ng/ml. Reactivity was also confirmed by direct radioimmunoassay and by complement fixation assays (see below).

Absorption Analysis. Two to ten million cells were washed in PBS and pelleted at 500×g in a 5×50 mm glass tube and allowed to react with an equal volume of ascites diluted to a concentration four times that needed to form 50% rosettes on positive cells: HL60 cells or the immunizing ANLL cells. (This was typically a dilution of ascites of 100,000–200,000.) The absorption proceeded for 30 min. at 4° C., and the mixture was again pelleted at 500×g. The supernatant was reacted with target cells lines in rosetting assays as described above.

Antibody-dependent Cellular Cytotoxicity (ADCC). Assays to determine if M195 was capable of mediating ADCC were conducted essentially as described by Welt et al. (35 Ref.b). Target cells were incubated in $^{51}$Cr for ninety minutes and then washed of free $^{51}$Cr. M195 antibody was added at concentrations of 1–100 μg/ml on ice, and fresh peripheral blood mononuclear cells added at effector to target ratios of 10–40/1. Cells were incubated at 37° C. for 6–18 hr and harvested using a Skatron cell harvester, and released $^{51}$Cr was counted in a Packard gamma counter. Detergent lysed cells were used as a 100% control, and isotype matched irrelevant antibody treated cells were used as a negative control.

Radioiodination and Radioimmunoassays. Purified antibodies were labeled with Na-$^{125}$I (New England Nuclear) using chloramine-T to start and sodium metabisulfite to stop the reaction. Specific activity was between 2 and 10 μCi/μg of protein. Immunoreactivity was between 40 and 60% as determined by serial binding to an excess of live HL60 cells. Radioimmunoassays were conducted on $5 \times 10^6$ live cells in 100 μl RPMI with 10% FCS and preincubated 15 min. with 2% heat inactivated normal rabbit serum to block nonspecific binding. Binding proceeded at 4° C. for 90 min followed by the tree washes with RPMI/FCS. Bound radioactivity was measured in the cell pellets in a Packard gamma counter.

Preparation of F(ab)'2 Fragments. One mg of purified immunoglobulin was reacted at 37° C. for 6 hr with immobilized pepsin beads (Pierce Chemicals) in acetate buffer at pH 4.5. The reaction was stopped by adjusting the pH to 8.8 and sedimenting the pepsin beads at 15,000×g for 1 min. Undigested immunoglobulins and Fc fragments were removed by reaction with Protein A Sepharose (Pharmacia). Purity of fragments was determined by SDS-polyacrylamide gel fractionation followed by Coomassie blue staining.

Competition Radioimmunoassay for Blocking Antigen in Serum. Serum from patients with hematopoietic neoplasms was obtained from fresh clotted blood and stored at −70° C. until use. The presence of blocking M195 antigen in sera was assayed by incubating 50 μl of freshly thawed serum and a dilution of $^{125}$I-labeled mAb M195 IgG for 20 min at 4° C. M195 IgG was at a concentration sufficient for 50% maximal binding to $5 \times 10^5$ HL60 target cells. The cells were then added and the incubation continued for 60 min at 4° C. followed by two washes with RPMI medium. Inhibition of M195 IgG binding was scored as the percent decrease in binding to HL60 as compared to mAb M195 incubated in the presence of 2% bovine serum albumin (BSA) in PBS and no competing sera.

Complement-mediated Cytotoxicity. Twenty-five μl of target cells at $2 \times 10^6$ cells/ml were mixed with 25 μl of complement and 25 μl monoclonal antibody at 4° C. The mixture was then incubated at 37° C. and occasional shaking for 45 min. Live and dead cells were enumerated using trypan blue exclusion as an indicator.

Guinea pig serum and baby rabbit serum were purchased from PelFreeze; human sera were obtained from volunteers. All complement sources were stored at −70° C. until use and not reused. Complement was used at the maximum concentrations not showing nonspecific lysis of the target cells: generally at 1:6–8 final dilution.

Indirect Immunoperoxidase and Immunofluorescence Assays. Histologically normal adult human tissues were obtained from surgical pathology specimens within 1–2 hr of resection. Several normal specimens of organs from several cases were used. Tissues were embedded in OCT compound after freezing in iopenthane/liquid $N_2$. Tissues were cut 4–8 μm thick, fixed in acetone, quenched with 0.1% $H_2O_2$, and blocked with either goat or horse sera. MAb M195 was used as supernatant, ascites, or purified IgG at 20 μg/ml. Positive and negative Ig controls were included in all studies. Goat anti-mouse IgG peroxidase conjugates (1:50 dilution) (Tago, Burlingame, Calif.) or biotinylated horse anti-mouse IgG with Avidin-biotin peroxidase complexes (Vector Laboratories, Burlingame, Calif.) were used as secondary reagents. Diaminobenzidine was used as a chromogen. For fluorescence studies, goat anti-mouse Ig fluorescein isothiocyanate conjugates (Becton-Dickenson) were used as secondary reagents.

Modulation of Cell Surface Antigen. Modulation of the cell surface antigen detected by mAb M195 after antibody binding was monitored by complement mediated cytotoxicity (36 Ref.b). HL60 cells were incubated with various concentrations of M195 IgG for up to 3 hr at 37° C. Additional antibody and rabbit complement were added at several time points and the amount of cell lysis was determined 45 min later.

Differentiation of HL60. A cloned variant of HL60, IF10 (34 Ref.b), and its differentiated monocytic variant (incubation with vitamin $D_3$ and phorbal myristate acetate for 3 days to promote monocytic maturation) were used (34 Ref.b). Both cell lines were kindly provided by Dr. Y. Cayre.

RESULTS

Distribution of M195 Antigen on Hematopoietic Cell Lines. mAb M195 was selected for detailed study from a group of several hundred hybridoma-produced antibodies generated from the fusion of a spleen from a mouse immunized with fresh live ANLL cells (FAB classification, M2). The antibody showed specific high titer binding in PA-rosette assays to the myeloid and monocytic cell lines. HL60, KG1, IF10, U937, and the monocytic variant of IF10 (Table 1). mAb m195 was weakly reactive with the erythroleukemic line K562 and not reactive with KG1a, an undifferentiated myeloid line. mAb M195 did not react with 18 lines of B cell origin at various stages of differentiation nor with 10 lines of T cell derivation. One null lymphocytic line, N-ALL-1, was weakly reactive. Activated B cells and activated T cells did not express antigen. Non-reactive cell lines were confirmed as negative by absorption assays which can detect about 1 ng of M195 binding in 1,000,000 cells; rosetting assays detect binding at antibody concentrations of about 1 ng/ml. mAb AJ2 was used as a positive control in these assays where most cells were M195 antigen negative. This panel of cell lines showed that among hematopoietic cells M195 was restricted to the nonlymphoid lineages: it was most highly expressed on committed myeloid and monocytic cell lines and more weakly expressed on erythroid and earliest myeloid cells.

TABLE 1

Reactivity of M195 with Hematopoietic Cell Lines

| Cell | M195 | AJ2 (positive control) |
| --- | --- | --- |
| Myeloid | WP | P |
| K562, HL60 | PO | PP |
| KG-1, KG1a | P | P |
| IF10 | | |
| Monocytic | | |
| U937, 1f10 | PP | PP |
| THP-1 | 0 | |

TABLE 1-continued

Reactivity of M195 with Hematopoietic Cell Lines

| Cell | M195 | AJ2 (positive control) |
|---|---|---|
| Pre-B cells | | |
| NALL-1, NALM-1 | 00 | P |
| NALM-6, NALM-16 | 00 | P |
| B cells | | |
| SK Ly-16, -18, Daudi, | 000 | P |
| ARA-10, SK DHL-2, Raji | 000 | PP |
| CCRF-SB, LICR/My-2 | 00 | P |
| BALL-1 | | |
| Myelomas | | |
| Oda, U266, RPMI 8266 | 000 | P |
| RCS, HAS, Brown | 000 | |
| EBV-transformed B cells (n = 15) | 0 | |
| T cells | | |
| T-45, CCRF-CEM, Molt 4 | 000 | P |
| TALL-1, MT-1, HUT-102 | 000 | |
| RPMI 8402, CCRF-HSB2 | 00 | |
| p12/chikawa, HPB-ALL | 00 | P |
| PHA blasts (n = 5) | 0 | |

P = positive; W = weakly positive; 0 = negative
*As determined by direct Protein A and mixed heme-adherence rosseting and absorption assays as described in the text.

Quantitative Analysis of Binding to Myeloid Cell Lines. In order to confirm the results of rosetting assays and absorption assays and to look at quantitative differences in the expression of the M195 antigen among the myeloid and monocytic cells a sensitive radioimmunoassay using direct binding of $^{125}$I-labeled purified M195 was used. Many of the hematopoietic cells have Fc receptors in addition to or instead of target antigen on their surfaces, and binding of radiolabeled IgG to these Fc receptors may confound the quantitative results of the radioimmunoassay. Therefore an F(ab')2 fragment of M195 was prepared and used in the assays to confirm the number of antigenic sites.

Figure 1A:
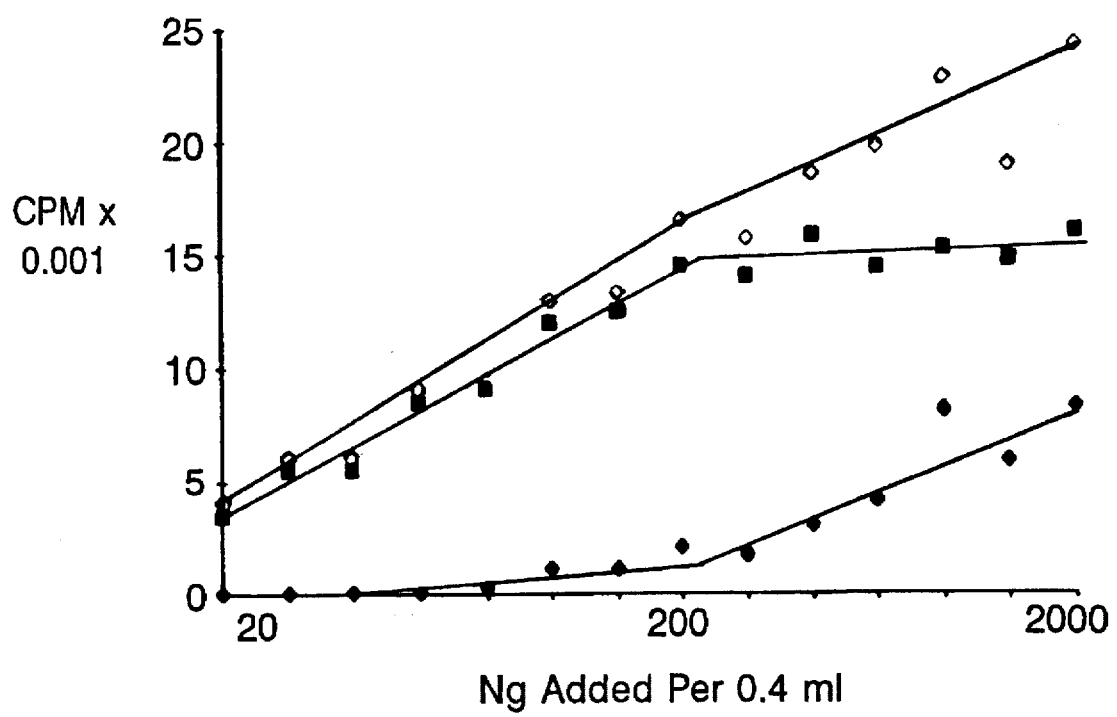
FIGS. 1A–1C. Radiobinding assays of M195 IgG and F(Ab)'2: Saturation and Scatchard analysis. Assays were conducted as described in Materials and Methods.
Figure 1B:
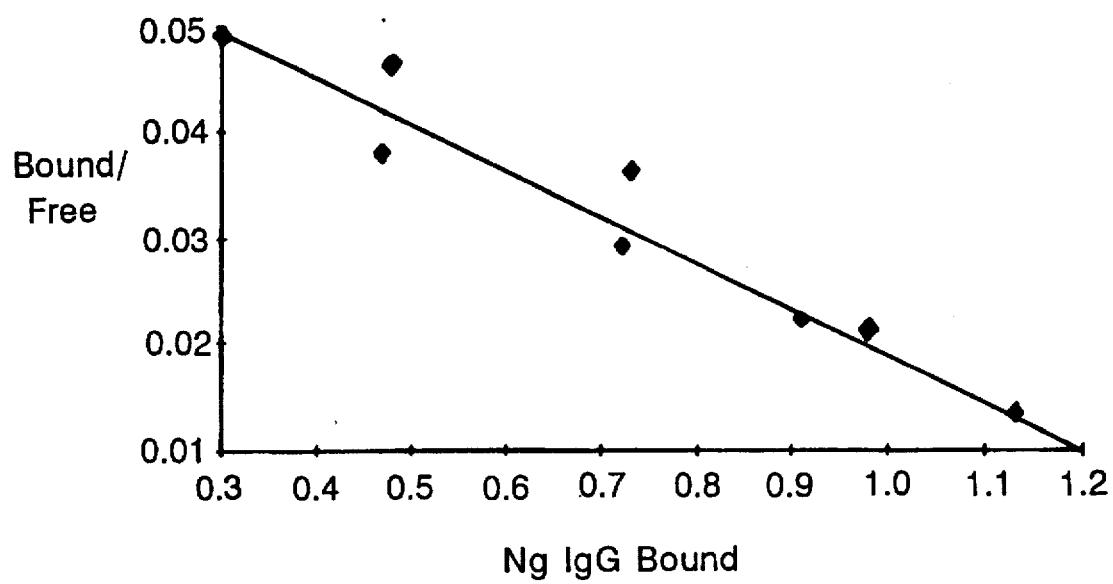
Figure 1C:
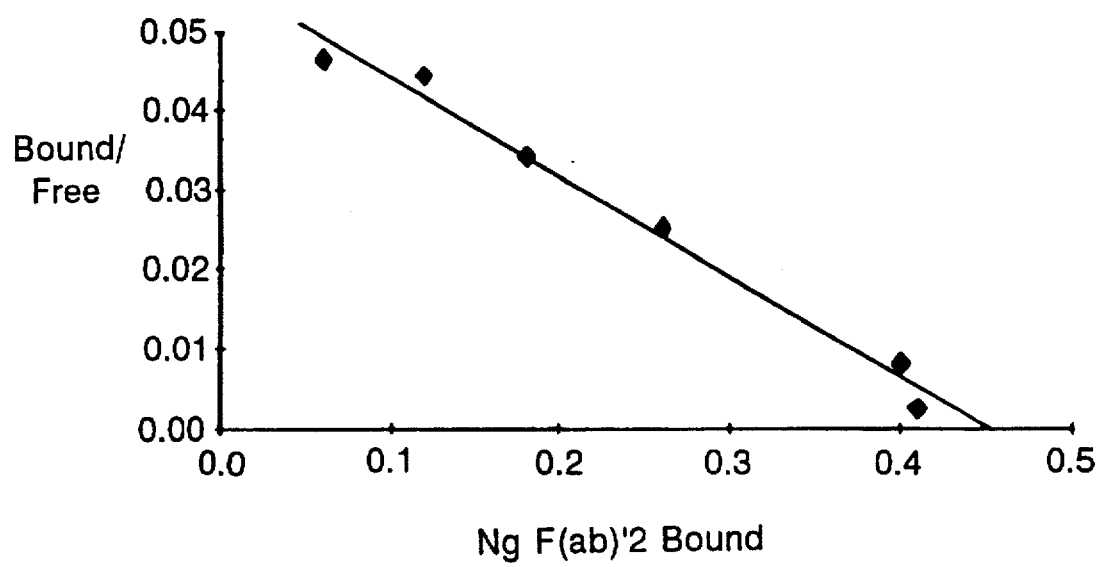

Binding of M195 IgG to HL60 showed saturation and specificity (FIG. 1A). Scatchard analysis showed an avidity of binding of $3 \times 10^9$ liters/mol (FIG. 1B) for the IgG. The number of binding sites calculated from this curve was approximately 100,000 per live HL60 cell. Scatchard analysis of several lots of M195 IgG on different passages of HL60 gave equivalent results. Analysis of purified F(ab')2 of M195 (FIG. 1C) showed similar avidity ($10^9$ liters/mol) cells and numbers of binding sites (10,000/HL60 cell), suggesting that binding activity was not significantly altered by protease digestion of the fragment.

Both the intact IgG and the F(ab)'2, fragment were used for radioimmunoassays on hematopoietic cell lines (FIG. 2). Non-specific binding (binding of $^{125}$I-M195 in the presence of excess unlabeled M195) under the conditions of this assay was approximately 200 pg (1600 molecules) per $5 \times 10^5$ cells. Therefore, only binding above this level was considered significant. Since the assay was done under saturating concentrations of M195 IgG or F(ab)'2, the total binding could be used to calculate the number of sites per cell. HL60, IF10, and U937 had 6000–12,000 sites per cell. KG1 had about 3000 sites per cell. Binding to KG1a and K562 was not above the background of nonspecific binding (1600 sites), and the nonmyeloid cell lines were negative. The assays confirmed the specificity of M195 for these myeloid and monocytic cells and showed that binding was not Fc receptor related. The three cell lines positive by rosetting and absorption had similar quantities of M195 antigen expression.

Reactivity with Fresh Normal Hematopoietic Cells. M195 was tested by absorption analysis for reactivity with live peripheral blood elements and cells derived from the major hematopoietic organs (Table 2). mAb M31 was used as a positive control. No reactivity was seen with M195 on any of these cell types.

Quantitative Analysis of Binding to Hematopoietic Cells. Direct radioimmunoassays were performed on fresh hematopoietic cells to confirm reactivity and quantitative binding (Table 2). Red blood cells, platelets, spleen cells, bone marrow cells, and peripheral blood mononuclear cells were negative. Polymorphonuclear leukocytes showed binding to the intact IgG at about 800 sites per cell above background but did not show significant binding to the F(Ab)'2 fragment suggesting that even this minimal binding was via the Fc receptors. Peripheral blood adherent cells (macrophages) were positive and binding to the F(Ab)'2 showed about 5000 antigen sites per cell. Binding to peripheral blood E-rosette negative cells was marginally above background, possibly due to the presence of a small percentage of macrophages contained in this population. With the exception of macrophages, the direct radioimmunoassays shown here confirmed the specificity analysis by absorption. The lack of reactivity with macrophages in the absorption assay may be due to the inability to obtain the large quantity of viable cells containing enough antigen necessary to absorb M195 (1,000,000 macrophages with 5000 antigen sites per cell would absorb only about 1 ng of antibody). Lack of binding in these radioimmunoassays would rule out the presence of some M195 positive cells within a large heterogeneous population as in bone marrow, for example.

TABLE 2

| | Assay Type | | |
|---|---|---|---|
| Cell Type | Absorption | Radio-immunoassay | Complement Lysis |
| T-enriched PBL[b] | — | — | — |
| B-enriched PBL | — | — | — |
| Granulocytes | — | — | — |
| Adherent monocytes | — | — | + |
| Platelets | — | — | ND[c] |
| Red blood cells | — | — | ND |
| Nonadherent PBMC | ND | — | — |
| Splenic T enriched | ND | — | — |
| Splenic B enriched | ND | — | — |
| Splenic mononuclear | — | ND | —[d] |
| Bone marrow mononuclear | — | — | —[d] |
| Lymph node mononuclear | — | ND | ND |
| Fetal thymocytes | — | ND | ND |

[a]Conducted as described in the text
[b]PBL = peripheral blood lymphocytes;
PBMC = peripheral blood mononuclear cells.
[c]ND = not done
[d]Nonadherent cells Complement-mediated Cytotoxicity Assays. Complement-mediated cytotoxicity was also used to confirm specificity. Assays were first done to determine if mAb M195 was capable of killing cells in the presence of rabbit, guinea pig, and human sera as sources of complement. Enzyme-linked immunosorbent assays showed mAb M195 to be an IgG2a class immunoglobulin, which is generally able to fix complement. Using HL60 as targets, M195 was capable of killing cells in the presence of guinea pig and rabbit complement but not human complement. In the presence of human complement, killing rarely occurred and was only 10–15% above background at its highest. Cell lines not expressing the antigen were not killed. No killing occurred in the absence of antibody or a source of complement.

Figure 3:
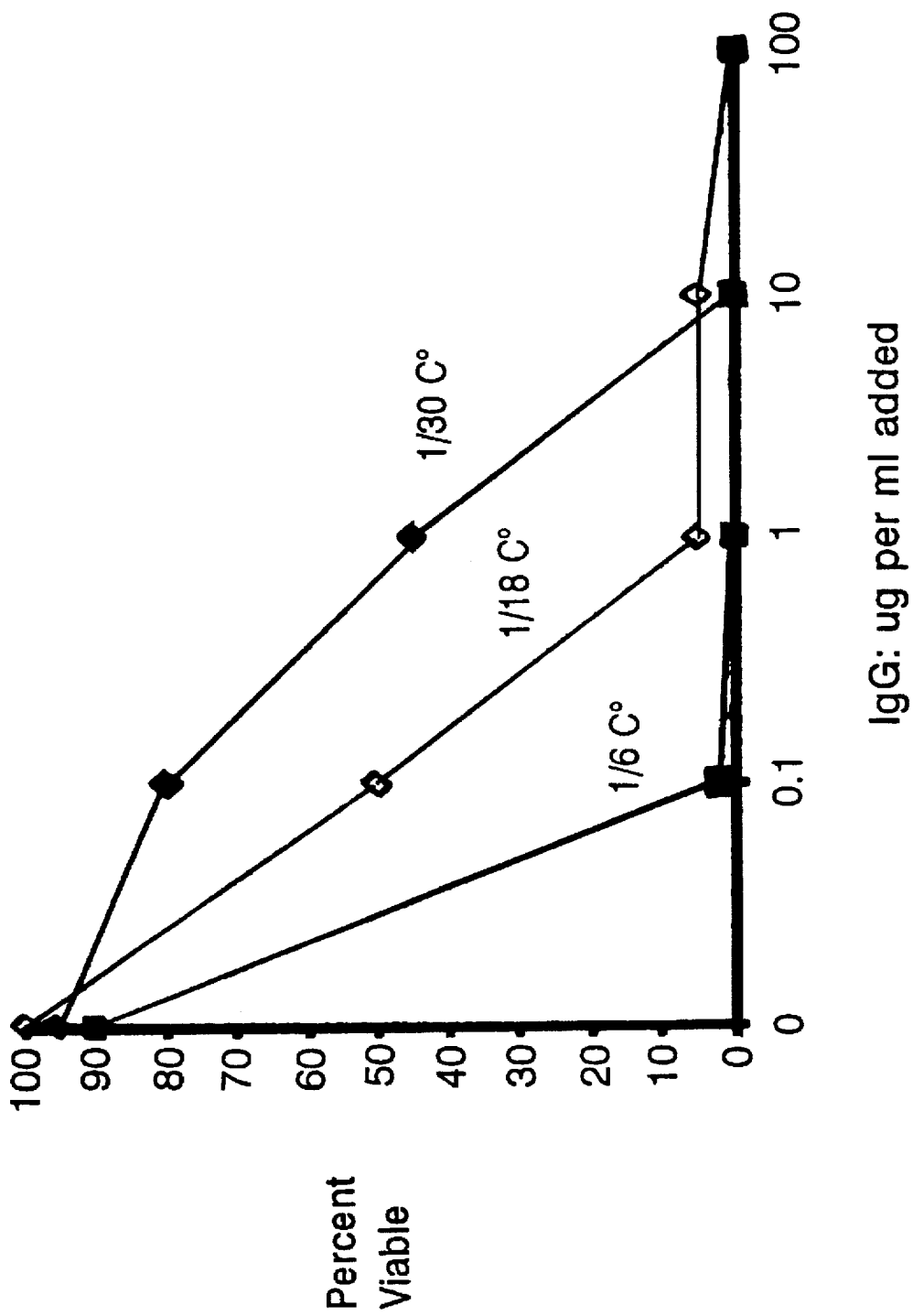
FIG. 3. Complement cytotoxicity by M195 IgG on HL60 cells using rabbit complement. The concentration of rabbit complement is shown in the figure: final dilution of ⅙ (■), ⅟₁₈ (◊), and ⅟₅₀ (♦). The assay was conducted as described in Materials and Methods.

Cytotoxicity was antibody concentration dependent and complement concentration dependent (FIG. 3). However, at concentrations of 10 µg/ml or greater of M195, nearly all cells were killed even with rabbit serum diluted 30-fold.

The complement assay was used to confirm the specificity analysis derived from the absorption assays and radioimmunoassays (Table 2). Complement assays are not confounded by Fc receptor binding and are able to determine percentages of cells within a large population which are antigen positive. Assays were conducted at 10 and 100 µg/ml M195 with rabbit serum diluted to 1:18 final concentration. HL60 and fresh monocytic leukemias were used as positive controls and B cell lineage RAJI cells and chronic lymphocytic leukemia cells were used as negative controls. Complement and antibody alone controls were also included. Background killing was between 1–55 in the controls without antibody or complement and 5–10% in the spleen E-rosette negative cells. Because of this background of several percent, it is not possible to determine if positive cells are present in a sample at this level or lower.

Only one population of mature normal hematopoietic cells showed killing above background using M195 and rabbit complement: peripheral blood adherent cells. Among three samples of adherent cells, 35–50% of cells were killed, showing that a subpopulation of these cells expressed the M195 antigen. This assay confirmed the radioimmunoassay data.

In chronic myelogenous leukemia (CML) mononuclear cells, a low percent of cells (5–6%) were killed above background (not shown). The cells comprising the CML mononuclear cell population include blasts through band forms with a predominance of the more mature myeloid cells. Morphologic analysis of these cells before and after antibody and complement treatment did not show which cells, if any, had been selectively killed. Because peripheral blood cells from patients with CML represent the full spectrum of maturing myelogenous cells, this lack of significant cytotoxicity confirms the lack of reactivity of M195 with the vast majority of adult myelogenous cells.

Reactivity of M195 and Differentiated HL60 Cells. IF10 cells and differentiated monocytic IF10 cells were provided by Dr. Yvon Cayre. One hundred percent of the IF10 cells became morphologically changed and adherent. The reactivity of M195 was tested by both rosetting and radioimmunoassays before and after differentiation. In the differentiated monocytic 1F10 cells there was a 40% loss of antigen expression by radioimmunoassay. Rosetting assays remained positive but the titer of binding dropped 10-fold. Quantitative binding to the differentiated 1F10 was similar to fresh normal adherent monocytes, suggesting the loss of antigen with monocytic differentiation among fresh hematopoietic cells was paralleled by this model line in vitro.

ADCC Assays. M195 did not show any ability to mediate ADCC against HL60 cells or U937 under the conditions described in Materials and Methods. These cells are the highest expressors of the antigen among those tested.

Reactivity of M195 with Nonhematopoetic Cell Lines. M195 was tested for reactivity with 70 cell lines derived from a wide spectrum of cancers (Table 3). No reactivity was seen. Monoclonal antibody AJ2 was included as a positive control and was positive in every case tested. Therefore, the M195 antigen appears to be restricted to hematopoietic cells.

TABLE 3[a]

Reactivity of M195 with Non-Hematopoietic Cell Lines

| | | M195 | AJ2 (positive control) |
|---|---|---|---|
| Astrocytomas | SK-MG-1,-2,-3. | 000 | P |
| | -4,-6,-7,-9 | 000 | P |
| | -12,-15,17,-23 | 0000 | P P |
| Bladder cancers | T-24, 253J,5637 | 000 | |
| Breast cancers | SK-BR-3,-5,-7 | 00 | |
| | BT-20,MCF-7 | 00 | P |
| Cervical cancers | CC-A, CC-B, HT-3 | 000 | PPP |
| | C41 | 0 | P |
| Choriocarcinomas | GCC-SV(c), Lu-75(c) | 00 | |
| Colon cancers | SW-403,-480,-620 | 000 | PPP |
| | -116,-1417 | 00 | PP |
| | HT-29,SK-CO-10 | 00 | PP |
| | CaCo-2,HCT-15 | 00 | PP |
| Lung Cancers | SK-LC-1,-4-6 | 000 | P P |
| | -8,9,-10,-17 | 0000 | P P |
| | Calu-1,-6,Sk-Lu-1 | 000 | PPP |
| | SK MES-1 | 0 | P |
| Melomas | SK MEL-13,23,-28 | 000 | PPP |
| | -29,-37,-93 | 000 | PPP |
| | -173, MeWo | 00 | P |
| Neuroblastomas | SK-N-MC,PNDW | 00 | PP |
| Ovarian cancers | SK-OV-3,OV-2774 | 00 | P |
| Pancreatic | ASPC-1,-2 | 00 | PP |
| Renal cancers | SK-RC,-1,-2,-7 | 000 | P |
| | -8,-9,-20,-28, | 0000 | PP |
| | -29,-45,-48 | 000 | PPP |
| Uterine cancer | ME 180, SK UT-1 | 00 | PP |

[a]Conducted as described in the text

Figures 4A, 4B:
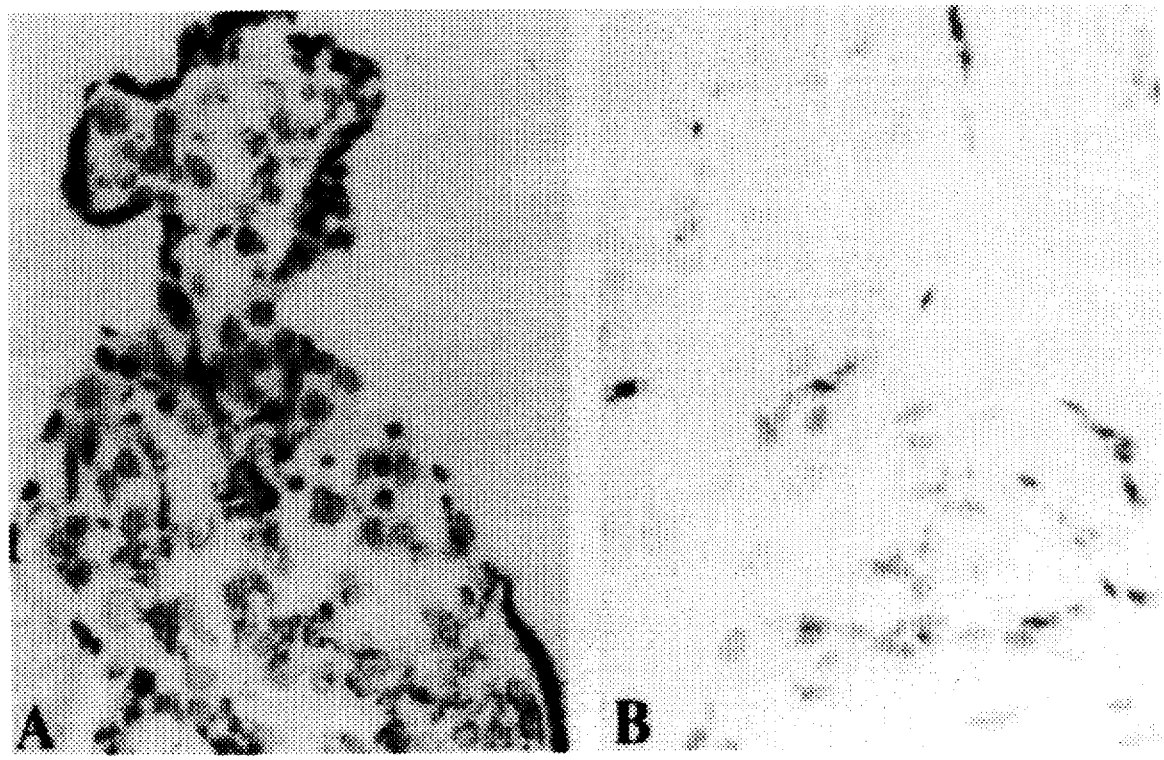
FIG. 4A and 4B. Indirect immunoperoxidase assay of M195 on trophoblast cells.

Tissue Distribution of M195. The reactivity of M195 with human tissues was determined in indirect immunofluorescence and indirect immunoperoxidase assays on fresh frozen tissue (Table 4). Among 25 different tissue types, reactivity was seen only with trophoblast. This reactivity was predominantly cytoplasmic (FIGS. 4A and 4B). These data on fresh tissue are consistent with the specificity data obtained from the assays with cell lines above.

TABLE 4

Tissue Distribution of M195[a]

| Tissue | Fluorescence | Peroxidase |
|---|---|---|
| Adrenal | 0 | 0 |
| Bladder | 0 | 0 |
| Blood vessels | 0 | 0 |
| Brain | 0 | 0 |
| Breast | 0 | 0 |
| Capillaries | 0 | 0 |
| Cervix | 0 | 0 |
| Colon | 0 | 0 |
| Heart | 0 | 0 |
| Kidney | 0 | 0 |
| Liver | 0 | 0 |
| Lung | 0 | 0 |
| Lymph node | 0 | 0 |
| Ovary | 0 | 0 |
| Pancreas | | 0 |
| Placenta | 0 | 0 |
| Prostate | 0 | 0 |
| Skin | 0 | 0 |
| Small Intestine | 0 | 0 |
| Stomach | 0 | 0 |
| Testis | 0 | 0 |
| Thyroid | 0 | 0 |
| Trophoblast | | P |

TABLE 4-continued

| Tissue Distribution of M195[a] | | |
|---|---|---|
| Tissue | Fluorescence | Peroxidase |
| Ureter | 0 | 0 |
| Uterus | 0 | 0 |
| HL60 (positive control) | P | P |

0 = negative; P = positive staining
[a]Conducted as described in the Materials and Methods M195 Reactivity with Fresh Leukemias. M195 reacted with most myelogenous leukemias and rarely with lymphoid leukemias in rosetting assays. Because of the nature of the rosetting assay, it was not possible to determine which cells were reactive or what percentage of blasts were positive. These issues and a detailed analysis of the specificity and activity of M195 in comparison to standard cell surface markers are presented in the accompanying paper (30 Ref.b).

M195 Blocking Antigen in Serum. In order to determine if the M195 antigen was shed into sera from hematopoietic cells, sera from people with a variety of leukemias and lymphomas or from healthy individuals were tested for soluble antigen capable of blocking of the binding of radiolabeled mAb M195 to HL60 cells (Table 5). Three of 39 human sera blocked binding significantly. The blocking was not complete. One serum was from a patient with CML. Two sera of six patients with acute lymphocytic leukemia partially block binding. The leukemia cells from both of these patients were not reactive with M195 antibody suggesting that the blocking antigen was not shed from these cells or that the blocking activity was not specific. These data suggest that M195 antigen in the serum would not be capable of preventing mAb M195 from reaching target cells. Because the sensitivity of this assay is about 200 ng/ml of M195, it is possible that M195 is expressed at lower levels than this in sera. In addition, monovalent antigen with low avidity for the M195 IgG may be present but unable to block binding.

TABLE 5

| M195 Blocking Factors in Sera of Patients with Leukemia | | |
|---|---|---|
| Serum Source | Number Tested | Number Blocking[a] |
| Normal | 6 | 0 |
| AML | 13 | 0 |
| CML | 6 | 1 (52%)[b] |
| ALL | 6 | 2 (56%,67%) |
| NHL/CLL | 8 | 0 |
| Rabbit, mouse, horse | 5 | 0 |

[a]A serum able to reduce by 50% or more, direct binding of 200 ng/ml radioiodinated M195 to HL60 target cells.
[b]The percent reduction by each positive serum.

Figure 5:
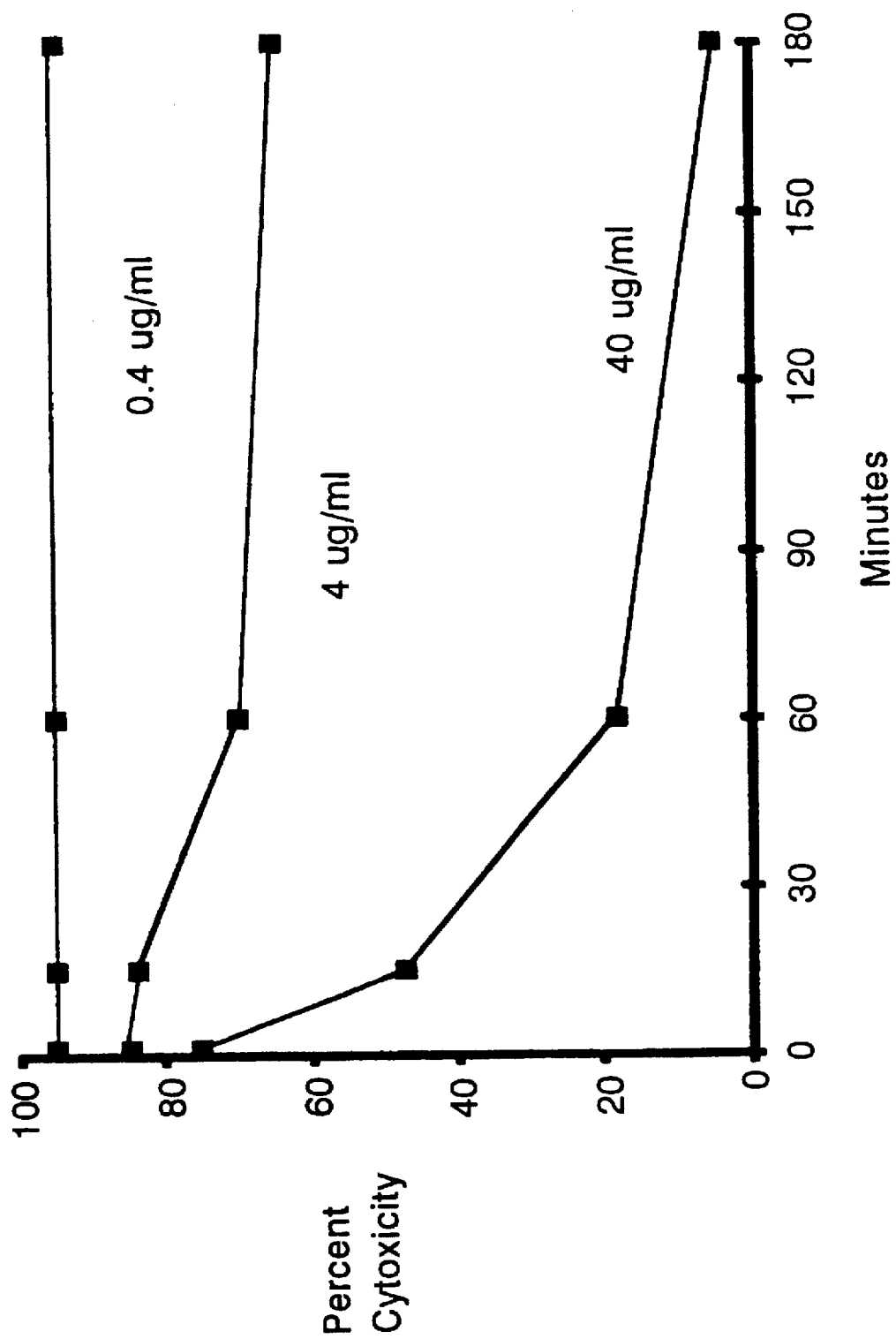
FIG. 5. Antigenic modulation after exposure of HL60 cells to mAb M195. The assay was conducted as described in Materials and Methods. M195 IgG was added at the concentrations shown in the figure and allowed to incubate at 37° C. for times indicated on the X axis. Cells were then tested for lysis by an additional aliquot of M195 IgG with rabbit complement at 37° C. for 45 min. Cytotoxicity after this second addition is shown on the y axis.

Antigenic Modulation. The ability of M195 to induce modulation of the antigen from the surface of HL60 cells was studied using complement-mediated cytotoxicity. HL60 cells were reacted with M195 at various concentrations, and the ability of M195 to kill the cells with added rabbit complement was measured versus time (FIG. 5). At the highest antibody concentrations complete modulation occurred within 3 hr. That is, the addition of complement to cells preincubated with mAb M195 for 3 hr resulted in no killing. Modulation was incomplete in cells exposed to lower mAb IgG concentrations. Other studies (to be published elsewhere) demonstrated that the modulation occurred via antigen internalization after antibody binding.

Biochemical Nature of the M195 Antigen. Treatment of HL60 cells with 100° C. for 1 min eliminated all binding activity in radioimmunoassays and rosetting assays. This suggested that the antigen epitope is carried on a protein. However, treatment with trypsin, protease, and neuraminidase had no effects on binding of mAB M195 to HL60 cells. These experiments, therefore, did not confirm the biochemical nature of the antigen. Repeated attempts to immunoprecipitate the antigen for $^{35}$S-methionine-labeled cells or cells surface-labeled with iodine-125 using lactoperoxidase were unsuccessful. Wester immunoblotting on HL60 extracts were also negative. Although we were unable to identify the target, other data shown in the accompanying paper (30 Ref.b) indicated that the antigen was carried on the CD33 protein.

DISCUSSION

This paper details the specificity of a new mouse mAb, M195, which is reactive with myelogenous leukemias, early myeloid cells and some monocytic cells. Qualitative and quantitative analyses of the mAb's binding, its biological activity, and its immunological functions are described.

Since two potential uses of M195 are diagnosis and in vivo therapy of ANLL, a comprehensive definition of its reactivity with all tissues and cells of the body was undertaken. Several assays were used in the specificity analysis of M195 on fresh cells and cell lines. Rosetting assays which are sensitive enough to detect 1 ng of mAb M195 per ml were used initially for specificity analysis. Direct radioimmunoassays using iodine-125 IgG and F(Ab)'2 were used next in order to quantitate the number of antigen sites expressed on various positive cells. The F(Ab)'2 has the advantage of defining non-Fc receptor binding quantitatively. Finally, a complement fixation assay was used to analyze reactivity. Since biological activity after binding to antigen in an appropriate fashion is required in this assay, the effects of nonspecific binding are reduced. Indirect immunofluorescence followed by confirmation with indirect immunoperoxidase assays were used to define M195 antigen expression on a broad spectrum of normal tissues. These results supported data obtained from the rosetting and absorption analysis on cell lines. Because the tissues were frozen sectioned and fixed, binding to cytoplasmic as well as membrane antigen could be detected in these assays.

M195 was found to bind specifically only to myeloid cell lines and monocytic cells. Lymphoid cells, including peripheral blood T and B cells, lymph node, spleen, and bone marrow cells, T and B cell lines representing pre-B, early B, B, and late B cell stages and T cell leukemias, and activated fresh B and T cells, did not express the M195 antigen. Red cells and platelets were also negative. Among 95 nonhematopoietic cell lines and nonhematopoietic tissues, only trophoblasts were reactive with M195. This activity appeared to be cytoplasmic. The presence of myeloid antigens in the cytoplasm of choriocarcinoma cells but not normal trophoblast has been reported (37 Ref.b), but its significance is unknown.

With the myelomonocytic lineage, the distribution of M195 antigen was even further restricted. Polymorphonuclear leukocytes were not reactive nor could significant binding be demonstrated in normal bone marrow mononuclear cells. A small percentage of cells from the peripheral blood mononuclear cells from patients with chronic myelogenous leukemia were positive. These samples contain largely granulocytic percursors up to the band stage. The lack of reactivity with polymorphonuclear leukocytes and this slight reactivity with CML suggests that the vast majority of mature and precursor myeloid cells do not express M195 antigen. In contrast, myeloid leukemia lines and fresh myeloid leukemias were strongly positive. Cell lines representing the earliest myeloid cells or erythroid cells were either negative or less positive than the myeloid cell lines representing later leukemias. These data place the M195 antigen expression to cells in the early to middle part of myeloid differentiation: the antigen is not present at first and is lost as the cells mature toward granulocytes.

Among monocytic cells, M195 reacted with both monocytic leukemia lines and a fraction of mature peripheral blood adherent cells. It was present on the HL60 variant, IF10, and in reduced amounts after monocytic differentiation of IF10 with vitamin D3 and phorbal esters. Likewise, AMOL blasts contained about 10,000 sites (30) compared to macrophages with 5000 sites. Therefore, like its expression on granulocytic precursors, the expression of the M195 antigen or monocytic cells appears to be maturation dependent.

Analysis of quantitative binding to HL60 cells gave an avidity of binding of the M195 IgG of $3 \times 10^9$ liters/mol. Binding was saturable and cell number dependent. These data showed that positive cell lines expressed about 10,000 antigen sites per cell. Therefore, M195 was rather weakly expressed compared to many other cell surface antigens. Although we have been unable to identify the target antigen of mAb M195, several of its features suggest it is a polypeptide. The antigen is heat labile; there are small numbers expressed on the surface. The antigen is rapidly modulated after antibody binding, and the antigen was detected by an IgG2a (which is this laboratory rarely identify carbohydrate).

The extremely restricted expression of this antigen among the cell types tested, the biochemical features noted above, including rapid modulation and internalization, and the small number of sites per cell all suggested that the M195 target may be a receptor important in growth and differentiation of myeloid progenitors. However, studies of the effects of M195 alone on the growth of myeloid cell lines, peripheral blood mononuclear cells (data not shown), and colony forming units (30 Ref.b) have not so far shown any stimulating or inhibiting effects of the mAb.

mAbs reactive with restricted myeloid antigens may be useful in a least four areas.

A) Study of the Growth and Differentiation of Myeloid and Monocytic Cells. Of the many antigen and antibody systems that have been described in myelomonocytic differentiation, three systems which have defined different states of myeloid maturation have been most widely studied: the CD34 system (mAbs MY10, 12.8, 3C5) (19–21 Ref.b) which identifies a gp115 found on the earliest hematopoietic progenitors, both lymphoid and myeloid, and which rapidly disappears upon differentiation is also found on some non-hematopoietic tissues including endothelium. mAbs to this antigen have been used to purify progenitors for reconstitution of bone marrow (18 Ref.b). The CD33 antigen system (mAbs MY9, L4F3, L1B2) (24–27 Ref.b) identifies a gp67 (17 Ref.b) restricted to early myeloid and monocytic cells. It is absent from the earliest hematopoietic progenitors and other normal tissues and has been used to eliminate leukemia cells, while sparing the ultimate progenitors, from bone marrow. The CD15 antigen system (multiple mAbs) identifies the Lewis X antigen found on granulocyte colonies from the day 7 stage on and increases expression as cells mature to the polymorphonuclear cell. The antigen is also widely distributed throughout normal tissues (38 Ref.b).

The distribution of the M195 antigen detailed in this paper shows it to fall into the myelomonocytic-restricted second category. Competition binding studies and binding to CD33 transfectants (discussed in Experiment 2 and 30 Ref.b) demonstrated that M195 was carried on the CD33 protein. However, cotyping on fresh leukemias showed that the antigen detected by mAb M195 was not identical to the other CD33 antigens (30 Ref.b).

B) Diagnosis of Hematopoietic Neoplasms. mAbs useful in diagnostic applications must be lineage specific, but not necessarily stage specific. For this reason, the CD34 antigen which is also present on lymphoid cells is less useful than the myelomonocytic antigen systems CD13 and CD15 or the monocytic specific antigens CD14 (27, 39, 40 Ref.b). M195 was restricted to myelomonocytic cells and is useful in the diagnosis of ANLL.

C) Purging of ANLL from Bone Marrow. In order to be useful in bone marrow purging, in addition to being myelomonocytic specific, the mAb must spare the ultimate progenitor cell. Reactivity with other tissues outside of the bone marrow is not important. The ability to fix complement is important but new methods to kill cells with toxins (41 Ref.b) or remove them with magnetic beads (42 Ref.b) may reduce this requirement. CD15 antibodies have proven most useful in this application and are in clinical trials currently (12 Ref.b). CD33 antibodies may be even more useful, if adequate recovery of the bone marrow progenitors can be assured. M195, which rapidly and efficiently kills leukemic cells with rabbit complement, can be successfully applied to this problem. (Lemoli R. M., Gulati S. C., Scheinberg D. A., Gasparetto C., Moore M. A. S., Clarkson B. D., Gee T., Autologous Bone Marrow Transplantation in Acute Myelogenous Leukemia (AML): In Vitro Treatment with Myeloid-Specific Monoclonal Antibodies (MoAbs) and Drugs in Combination. Blood 74(7):suppl,p280a abstract) (1989) see Experiment 5). Because the antigen can also be found on clonogenic neoplastic cells, the mAb can also be used to treat lymphoid neoplasms (Hudson, Anne-Marie, Makrynikola, V., Kabral A., Bradstock K. F., Immunophenotypic . . . Blood, 74(6):2112–2120 (Nov. 1, 1989).

D) Therapy with mAb in Vivo. This application is most difficult as it optimally requires limited reactivity with normal tissues, in addition to the criteria described above. Of the many antigen systems described for myelomonocytic cells, CD33 appears most suited for this application in vivo. M195 may be used in application, but its demonstrated lack of cytotoxicity in the presence of human complement or PBMC in vitro might require that the mAb carry a cytotoxic isotope or toxin to be effective. Since the antigen and antibody are rapidly internalized, this therapeutic modality is feasible and investigations of this application have now demonstrated delivery of antibody and conjugated isotope to leukemia cells in the blood and bone marrow (Scheinberg D. A., Lovett D., Divgi C. R., Berman E., Finn R., Graham M. C., Pentlow K., Clarkson B. D., Gee T. S., Larson S. M., Oettgen H. F., Old L. J., A Phase I Trial of Monoclonal Antibody M195 (Anti-CD33) In AML: Pharmacology, Toxicity, Radiolocalization, Dosimetry, ASCO Abstract, to be published in May, 1990) (Protocols). (Hudson, Anne-Marie, Makrynikola, V., Kabral A., Bradstock K. F., Immunophenotypic . . . Blood, 74(6):2112–2120 (Nov. 1, 1989).

EXPERIMENT 2

(Ref.a)

In experiment 1 we described a mouse monoclonal antibody, M195, which detects an antigen found on early myeloid cells, monocytes, and ANLL cells but not on cells of other hematopoietic or nonhematopoietic lineages (16 Ref.a). The antigen described has several features in common with the myelomonocytic antigen CD33 (4.5 Ref.a) which is found on early myeloid cells and ANLL cells but not on the ultimate progenitor cells (17 Ref.a), a characteristic which may allow selective killing of ANLL cells (18 Ref.a). In this study, we describe the specific reactivity of M195 with ANLL among 227 different fresh hematopoietic neoplasms. The reactivity was similar but not identical to that of MY9 (CD33). Cross-blocking of the binding of these two antibodies to target cells was found. In combination with MY9, M195 showed specificity in diagnosing ANLL by flow cytometry of clinical specimen. M195 bound to most CFU-GM, as measured by colony forming assays. This pattern of reactivity of M195, together with its lack of reactivity with adult tissues (16 Ref.a) make mAb M195 useful in therapeutic trials in humans.

MATERIALS AND METHODS

Monoclonal Antibodies. M195, a mouse IgG2a, was prepared in this laboratory as described in the Experiment 1 (above). The following mAbs were purchased from Coulter Immunology (Hialeah, Fla.): MY9, an IgG2b, (CD33); B4, and IgG1 (CD19); B1, an IgG2A (CD20); $I_2$ or $I_3$, IgG2As (anti-HLA-DR); MY4, an IgG2b (CD14); and MY7, an IgG2b (CD13). These were either obtained as fluorescein isothiocyanate conjugates or pure immunoglobulins. The following mAbs were purchased from Becton-Dickinson (Mountain View, Calif.): MY10, an IgG1 (CD34) and goat anti-mouse Ig fluorescein isothiocyanate conjugate of F(ab)'2. L4F3, IgM (CD33) ascites was the gift of Dr. Irwin Berstein. M31, IgM, (CD15) and OKB7, IgG2B (CD21) from a hybridoma provided by Ortho Biotech (Raritan, N.J.) were prepared in this laboratory.

Flow Cytometry. Five million fresh live mononuclear cells from bone marrow or blood from patients on the Hematology-Lymphoma Service at Memorial Hospital were incubated in 0.1 ml final volume with the fluorescein conjugated monoclonal antibodies for 30 min at 4° C. and then washed twice and fixed with 0.1% paraformaldehyde before analysis. For indirect immunofluorescence, after the primary antibody incubation for 30 min at 4° C., 50 µl of goat anti-mouse fluorescein conjugate were added for 30 min, followed by washing and fixing. In some samples, whole blood was analyzed by direct immunofluorescence using the Q prep method (Coulter). Ten thousand cells were analyzed on either an EPICS C or an EPICS profile (Coulter) flow cytometer. Blasts were gated for analysis. Samples containing greater than 25% positive cells (using an isotype matched control Ig to designate the upper limit of negative fluorescence intensity) were scored as positive.

Radioimmunoassays. M195 IgG2a was purified by protein A affinity chromatography, radiolabeled with iodine-125, and used in direct radioimmunoassays on live leukemia and bone marrow cells as described before (16 Ref.a). M195 was labeled to 2–10 µCi/µg protein. Specific binding was determined by subtracting the amount of M195 IgG2a bound in the presence of an excess of unlabeled M195 IgG2a. Non-specific binding was about 400 pg per million cells (1600 sites per cell). Binding at this level or below was therefore considered insignificant.

Morphological Designation of Leukemias. Acute leukemias in patients on the Leukemia Service at Memorial Hospital were classified according to the French-American-British (FAB) criteria (19 Ref.a) and were reviewed by at least one of the authors. Undifferentiated cells with negative histochemical stains which did not appear to be lymphoid and which did not meet FAB criteria for other diagnoses were classified as M0 (two cases only). Bone marrow aspirates and peripheral blood smears were stained with McNeil's tetrachrome (Polyscience, Warrington, Pa.) for morphology. Histochemical analysis included staining with Sudan black B and/or peroxidase and periodic acid Schiff, alphanaphthylbutyrate and ASD chloroacetate esterase, acid phosphatase, terminal deoxynucleotidyl transferase (Tdt). Potential B cell neoplasms were analyzed by mouse red cell rosetting and by indirect immunoperoxidase for immunoglobulin products. The presence of the sheep red blood cell receptor on T cells was determined by rosetting at 37° C. and 4° C. (and by monoclonal antibody by flow cytometry).

Determination of Bone Marrow Colony-forming Units. Bone marrow mononuclear cells were assayed for colonies derived from CFU-GM, CFU-GEM, and BFU-E as described (13 Ref.a). Cultures consisted of Iscove's modified Dulbecco's medium (Gibco, Grand Island, N.Y.) with 24% fetal calf serum, 0.8% deionized bovine serum albumin (Sigma Chemical, St. Louis, Mo.), $10^{-4}$M 2-mercaptoethanol (Sigma Chemical). 1 U partially purified human urinary erythropoietin (49 U/mg) (Toyobo, New York, N.Y.), 10% MO T cell line conditioned media, and 1.3% methylcellulose. Cultures were prepared in quadruplicate and scored on days 7 or 14. In some assays, adherent cells were depleted first by plastic adherence at 37° C. for 90 min.

Antibody mediated complement cytotoxicity of colony forming units was determined by incubating the marrow mononuclear cells first in excess monoclonal antibody (10–100 µg/ml) and low toxicity baby rabbit complement (Pel freeze), at a final dilution of 1:8, for 30 min at 37° C. followed by two washes with media. Alternatively, human serum was used as a complement source.

Preparation of Purified Normal Progenitor Blasts. Normal bone marrow cells were depleted of accessory and maturing cells to obtain enriched populations of progenitors by negative selection using density separations and a panel of monoclonal antibodies followed by immune rosetting or panning as described (13 Ref.a). The 12 antibodies reacted with cell surface antigens present on mature T, B, myeloid, and monocytic cells. Cells were then frozen in liquid $N_2$, and thawed once, then reseparated on Ficoll-Paque (Pharmacia, Piscataway, N.J.) before use.

RESULTS

Distribution of M195 on Hematopoietic Neoplasm. The binding of mAb M195 to mononuclear cells from 227 patients as measured by flow cytometry is shown in Table 1. M195 was found on the majority of myeloblastic leukemias; 80% of the positive ANLL cases had greater than 50% of cells positive for M195. Forty percent of positive cases had greater than 75% of cells positive for M195. Lymphoid leukemias, lymphoproliferative disorders, and other nonmyeloid samples were virtually always negative (4% of cases positive).

Figure 6:
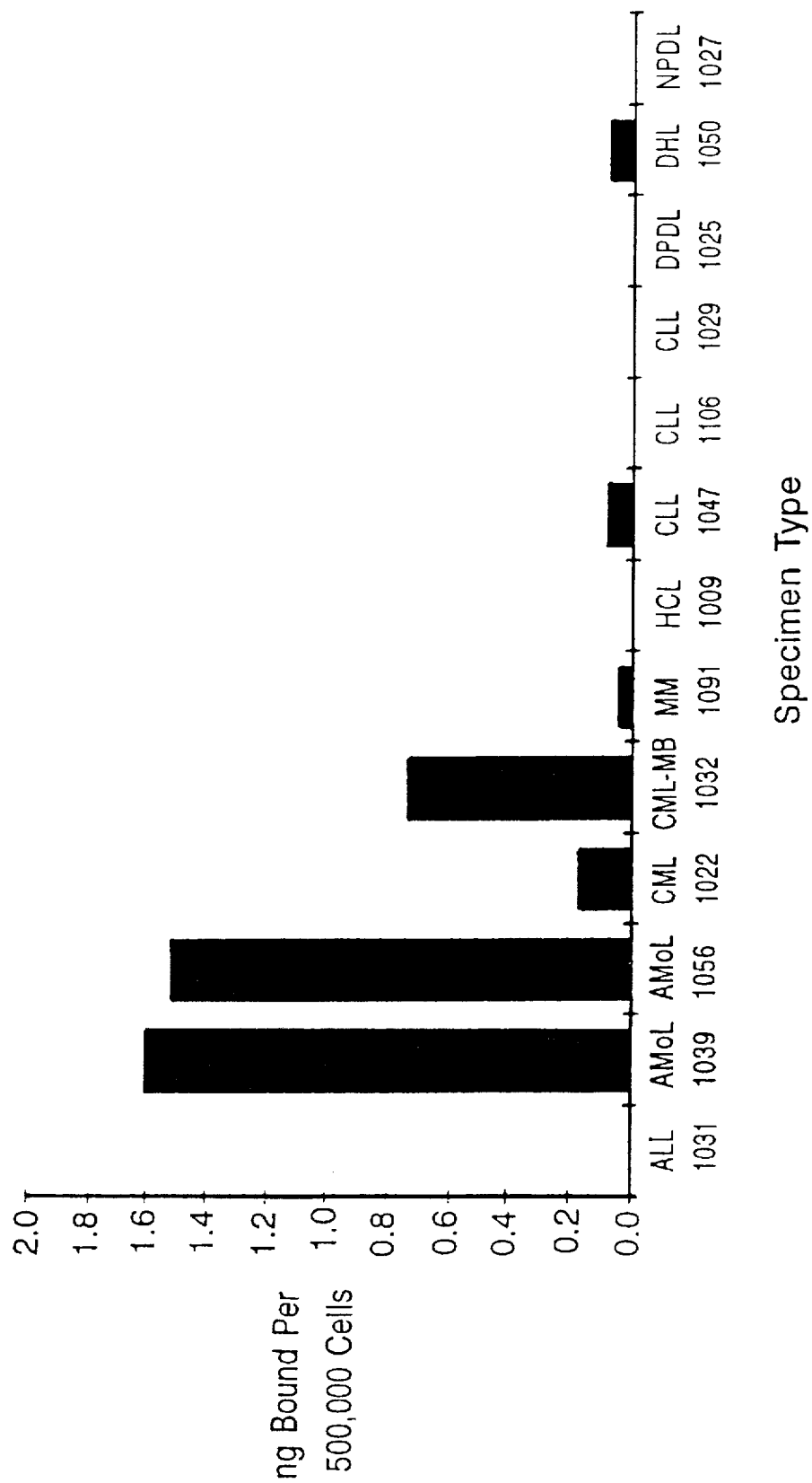
FIG. 6. Direct Radioimmunoassay for mAb M195 IgG on fresh hematopoietic neoplasms. The assay was conducted as described in Materials and Methods. The identities of the specimens are shown along the X axis; 1 ng bound per 500,000 cells is equivalent to 8000 IgG per cell. AMOL is acute monocytic leukemia; CML-MB is myeloblastic CML; MM is multiple myeloma; HCL is hairy cell leukemia; CLL is chronic lymphocytic leukemia; DPDL is diffuse poorly differentiated lymphoma; DHL is diffuse histiocytic lymphoma; NPDL is nodular poorly differentiated lymphoma; The lymphomas were suspensions made from lymph nodes. Background nonspecific binding was 0.2 ng bound. Only specific binding is shown.

A quantitative analysis of the total number of binding sites on several of the positive hematopoietic neoplasms was conducted by radioimmunoassay. Our accompanying study (16 Ref.a) showed that myelomonocytic leukemia cell lines expressed approximately 10,000 antigen sites per cell. The same quantity was seen on fresh ANLL cells from several patients (FIG. 6). Lymphoid leukemias and lymphomas, and chronic myelogenous leukemia (CML) cells in chronic phase did not express antigen on their surfaces.

TABLE 1

Distribution of M195 on Hematopoietic Neoplasms By Cytometry[a]

|  | No. Tested | No. Positive | (%) |
|---|---|---|---|
| Acute nonlymphoblastic leukemia | 54 | 34 | (63) |
| Tdt-positive cases only | 10 | 3 | (30) |
| Chronic myelogenous leukemia- |  |  |  |
| Accelerated and myeloblastic phase | 7 | 7 | (100) |
| Total myeloid, blastic cases | 61 | 41 | (67) |
| Chronic myelomonocytic leukemia | 3 | 3 | (100) |
| Myelodysplastic syndromes | 25 | 12 | (40) |
| Chronic myelogenous leukemia (chronic) | 17 | 7 | (41) |
| Acute lymphoblastic leukemia |  |  |  |
| Calla+ | 33 | 4 | (12) |
| Calla- | 8 | 0 |  |
| T-ALL | 5 | 0 |  |
| Chronic myelogenous leukemia- |  |  |  |
| Lymphoblastic phase | 5 | 0 |  |
| Total lymphoid, blastic cases | 51 | 4 | (8) |
| Lymphoproliferative disorders (T + B) | 19 | 1 | (5) |
| Normal, nondiagnostic, and other | 51 | 0 |  |
| Total cases | 227 |  |  |

[a]Conducted as described in the Materials and Methods

The expression of M195 was compared to the FAB classification of ANLL (Table 2). M195 was expressed in all subclasses of ANLL except M0 and M6. Since there were very few leukemias of these two classes, the significance of this is not clear. However, when both the M0 and M1 classes were pooled, only 3 of 14 (23%) were positive compared to 30 of 44 M2, M3, or M4 leukemias (68%).

TABLE 2

Distribution of M195 Antigen among FAB Morphological Subgroups of AML

| FAB Group | No. Tested | No. M195-Positive | (%) |
|---|---|---|---|
| M0 | 2 | 0 | (0) |
| M1 | 12 | 3 | (25) |
| M2 | 24 | 15 | (63) |
| M3 | 5 | 5 | (100) |
| M4 | 15 | 10 | (67) |
| M5a | 5 | 3 | (60) |
| M5b | 18 | 8 | (44) |
| M6 | 2 | 0 | (0) |
| M7 | 1 | 1 | (100) |

Tdt-positive ANLL (>320 ng/$10^8$ cells) also tended to be M195-negative (30%) compared to the Tdt-negative myeloid leukemias (74%). These data supported the suggestion from our earlier paper on cell lines that the M195 antigen was more highly expressed on early committed granulocytic precursor cells than on more undifferentiated earlier myeloid cells (16 Ref.a).

M195 was found on about a third of CML samples in chronic phase, all CML samples in myeloblastic or accelerated phase but not on lymphoblastic CML cells (Table 3A). Four of 46 acute lymphocytic (ALL) leukemias were M195-positive (Table 3B). These ALL samples were CALLA-positive pre-B leukemias. The total number of cells positive for M195 in these samples was rather low: 26%, 32%, 39%, and 42%. Other markers are shown for comparison. MY9 was present on five pre-B leukemias, with 27%, 28%, 35%, 35%, and 62% MY9-positive cells; four of these were different from those that were M195-positive. One case was 28% MY9-positive and 42% M195-positive. MY9 was also found on one of five cases of lymphoblastic CML (Table 3A).

TABLE 3A

Immunophenotype of Chronic Myelogenous Leukemia at Memorial Hospital

| | No. tested | M195 | My9 | My10 | My7 | My4 | Calla/B4 | Ia |
|---|---|---|---|---|---|---|---|---|
| CML chronic phase | 24 | 17 | 41 | 41 | 19 | 18 | 6 | 6 |
| CML accerlated and myeloblastic | 7 | 100 | 70 | 100 | 86 | 28 | ND | 86 |
| CML lymphoblastic | 80 | 5 | 0 | 20 | 100 | 50 | 0 | 80 |

TABLE 3B

Immunophenotype of Acute Lymphoblastic Leukemias at Memorial Hospital[a]

| ALL type | No. tested | Ia | My10 | B4 | B1 | M195 | My9 |
|---|---|---|---|---|---|---|---|
| Ia |  |  |  |  |  |  |  |
| CALLA+ | 33 | 82 | 58 | 91 | 52 | 12 | 15 |
| CALLA- | 8 | 88 | 88 | 100 | 0 | 0 | 0 |
| T-ALL | 5 | 0 | 0 | 0 | 0 | 0 | 0 |
| Total non-T ALL |  | 41 | 83 | 64 | 95 | 41 | 1012 |
| Total ALL | 46 | 74 | 57 | 85 | 37 | 9 | 11 |

[a]Conducted as described in Materials and Methods

A Comparison of M195 with CD33 Antigens. Our previous paper suggested that the distribution of M195 appeared similar to that described for CD33-reactive antibodies MY9 and L4F3. The protein target of M195 has thus far eluded detection (16 Ref.a). A comparison of M195 reactivity to other well characterized myeloid markers on the same leukemias is shown in Table 4 (this table does not include 30 leukemias that were not characterized by other markers that were included in Table 2). MY10, MY7, and MY4 were distributed among all subtypes in patterns dissimilar to M195. MY9 was strikingly similar to M195 in its pattern of distribution. An analysis of the concordance of M195 and MY9 in the flow cytometric studies on fresh, acute blastic leukemias (lymphoid and nonlymphoid) is shown in Table 5. In 93 cases of ANLL or acute lymphoid leukemias, either both markers were positive or both were negative. In 19 cases the binding differed, resulting in a concordance rate of 83% overall. This high, but not complete, concordance suggested that the M195 antigen might be related to or coexpressed with the CD33 antigen.

TABLE 4

Immunophenotype of FAB Subgroups of AML at Memorial Hospital[a]

| | No. | % Testing Positive for: | | | | |
|---|---|---|---|---|---|---|
| Group | tested | My10 | My7 | My9 | M195 | My4 |
| M0 | 2 | 100 | 100 | 0 | 0 | 0 |
| M1 | 5 | 80 | 50 | 60 | 40 | 0 |
| M2 | 15 | 67 | 33 | 73 | 73 | 7 |
| M3 | 4 | 100 | 50 | 100 | 100 | 75 |

TABLE 4-continued

Immunophenotype of FAB Subgroups of AML at Memorial Hospital*

| Group | No. tested | % Testing Positive for: | | | | |
|---|---|---|---|---|---|---|
| | | My10 | My7 | My9 | M195 | My4 |
| M4 | 10 | 70 | 40 | 80 | 70 | 44 |
| M5a | 3 | 100 | 33 | 100 | 67 | 0 |
| M5b | 12 | 58 | 45 | 75 | 58 | 17 |
| M6 | 2 | 50 | 100 | 50 | 0 | 0 |
| M7 | 1 | 100 | 0 | 100 | 100 | 0 |

*Conducted as described in Materials and Methods

TABLE 5

Concordance Data for M195 and My9 amoung 112 Blastic Leukemias

| Reactivity Pattern | No. of Cases |
|---|---|
| My9 + and M195+ | 38 |
| My9 − and M195− | 55 |
| My9 + and M195 − or My9 − and M195+ | 19 |
| Over all concordance | 83% |

Cross-blocking experiments using iodine-125-labeled M195 IgG or F(Ab)'2 binding to HL60 leukemia cells in the presence of excess concentrations of various immunoglobulins are shown in FIG. 2. Both MY9 and L4F3 (CD33-reactive), as well as the original M195 IgG, blocked binding of the $^{125}$I-M195. MY7 (CD13), M31 (CD15), and OKB7 (CD21) did not inhibit binding. These data further confirmed the association between the M195 antigen and CD33 antigens. In other experiments (not shown) excess unlabeled M195 was able to block binding of about 50% of FITC-labeled MY9 to HL60 cells as measured by flow cytometry.

Mab M195 was also tested by Dr. T. Look (St. Jude, Memphis, Tenn.) for reactivity with NIH-3T3 cells transfected with the DNA from myeloid cells and expressing the CD33 antigen (20 Ref.a). Both L4F3 (CD33) and MY9 (CD33) are reactive with these cells; M195 was reactive as well. This result, when taken in context with the nonidentical concordance data shown above, suggested that the M195 antigen was carried on the p67 (CD33) but was not the same as the previously described CD33 antigen epitopes recognized by L4F3 and MY9.

Diagnostic Utility of M195. MY9 is widely regarded as the standard marker for ANLL (21,22 Ref.a). We compared the diagnostic utility of MY9 with M195 either alone or together on 81 blastic leukemias of either myeloid or lymphoid origin (Table 6). Eighty-four percent of ANLL expressed either M195 or MY9, but each antibody alone failed to identify more than a quarter of cases. Among lymphoid cases either MY9 or M195 was occasionally expressed, but both antibodies were expressed together only once. In this case the reactivity was weak: 28% MY9+ and 42% M195+. Thus, the presence of both M195 and MY9 positivity on a leukemia sample had 98% specificity in defining that leukemia as ANLL.

TABLE 6

Diagnostic Utility of M195 and My9 among Blastic Leukemias
Positive Cases with the Indicated Marker(s)

| My9 | M195 Alone | Both M195 and My9 Alone | Either M195 and My9 |
|---|---|---|---|
| Sensitivity[a] in 61 Myeloblastic cases | 67% | 74% | 67% 8% |
| Specificity[c] in 51 lymphoblastic cases | 8% | 12% | 2% 20% |

[a]Antibody(s) should be positive in all cases
[b]Percent of cases positive by flow cytometry
[c]Antibody(s) should be negative in all cases Expression of M195 on Hematopoietic Colony-forming Cells. The expression of M195 on leukemia cells, but not on mature nonadherent peripheral blood cells nor on any detectable nonadherent bone marrow cells (16 Ref.a), suggested that M195 might be expressed on a small group of hematopoietic progenitors. The expression of M195 antigen on hematopoietic progenitors was studied by analyzing the recovery of bone marrow colonies after treatment of bone marrow mononuclear cells with M195 and rabbit complement (Table 7). Complement alone, antibody alone, and no antibody or complement treatments were used as negative controls. Antibody to human IA antigen (gift of Dr. J. D. Griffin) was used as a positive control. The number of CFU-GEMM recovered was not sufficient to obtain statistically significant data. In three of four experiments, M195 and complement eliminated almost all of the 14-day CFU-GM; burst forming unit erythrocytes were also killed, although the average recovery was somewhat higher.

TABLE 7

Recovery of Colonies after Treatment with Antibody and Complement

| | % Recovery of the Following Colonies | |
|---|---|---|
| Treatment | Day 7 Day 14 CFU-GM | CFU-GMBFU-E |
| Nil | 124[a] (111,136) | 126(139,104,111,110) | 103(143,83115,71), |
| M195 alone | 124(126,181,93,98) | 108(97,120) | 107(141,114,98,74) |
| Complement alone | 100[c] | 100100 |
| M195 plus complement | 6(10,1) 33(8,77,6,40) | 17(0,60,3,6) |
| Anti-IA plus complement | 0(0,ND[d]) 6(5,11,1,ND) | 1(0,2,0,ND) |

[a]Mean of all experiments shown
[b]Percent recovery of an individual experiment
[c]The "complement alone" treatment was considered to be 100% recovery, and other data on this chart were normalized to that value. Plating efficiency was between 0.10 and 0.15 percent
[d]ND = Not determined.

In order to determine the extent of expression of M195 on early hematopoietic progenitors, radioimmunoassays were conducted on highly purified blasts. The cells used were isolated by negative selection with a panel of 12 monoclonal antibodies and immunorosetting or panning followed by freezing and thawing once (13 Ref.a). These cells are morphologically blasts and represent a progenitor cell population 50–100-fold purer than bone marrow mononuclear cells. Five to fifteen percent of these cells typically form myeloid and erythroid colonies.

No binding of $^{125}$I-M195 above background was found in testing three different samples of these normal, early blast cells. A small percent of positive cells could escape detection using this assay.

Because these data suggested that M195 antigen was expressed on a minor population of bone marrow cells responsible for CFU-GM colonies, we attempted to identify these cells by positive selection with panning, immunomagnetic bead separation, affinity sepharose bead separation, and fluorescence-activated cell sorting. None of these methods selected out a M195-positive subpopulation. This may be due to weak antigen expression, antibody affinity, or other unknown problems.

Effects of M195 on Bone Marrow progenitors in the Presence of Human Complement. Because we anticipated possible use of M195 in vivo for therapy of ANLL, we studied the effects of M195 on CFU-GM and 5FU-E from normal bone marrow in the presence of human serum as a complement source (Table 8A). No killing of CFU-GM or BFU-E was seen at 14 days. The effect of the continued presence of M195 in bone marrow culture was also studied by adding the antibody to the methyl cellulose at days 1 and 5 after plating, with no added complement (Table 8B). These experiments were done to determine if the antibody had a growth stimulatory or inhibitory effect on progenitor cells in the marrow. No effects were seen. Similar growth studies of peripheral blood mononuclear cells and HL60 leukemia cells were also negative.

TABLE 8A

Effects of M195 on Hematopoietic Stem Cells in the Presence of Human Complement

| Treatment | No. of Colonies, Day 14 | |
|---|---|---|
| | CFU-GM | BFU-E |
| None | 116(100%)[b] | 154(100%) |
| Complement (C') alone | 102(100%) | 121(100%) |
| M195 | 132(113%) | 158(102%) |
| M195 + C' | 141(138%) | 127(105%) |

TABLE 8B

Effect of the Continued Presence of M195 on Colony Forming Cells[c]

| | | |
|---|---|---|
| Nil | 125(100%) | 188(100%) |
| M195 | 124(99%) | 168(89%) |

[a]Human serum was added at a final dilution of ⅙ as described for rabbit complement in Materials and Methods
[b]Quadriplicate control plate results are normalized to 100%
[c]M195 IgG was added directly to growing cultures as described in Materials and Methods

DISCUSSION

This paper describes the distribution of mAb M195's binding on fresh leukemia cells and early hematopoietic progenitors. In our accompanying paper (16 Ref.a) we showed that the M195 antigen was present on myelomonocytic leukemia cells and a fraction of monocytes but was not detectable on more mature myeloid cells present in the bone marrow or peripheral blood nor on nonhematopoietic cells and tissues. In this paper we extend the description of the M195 antigen and directly compare it to other well-characterized myeloid and monocytic antigens. Among 227 fresh hematopoietic samples studied, M195 antigen expression was largely restricted to differentiated ANLL. Undifferentiated and Tdt-positive ANLL were less likely to display antigen. However, FAB classification did not correlate specifically with M195 expression.

Quantitative analysis by radioimmunoassay showed that about 10,000 sites were expressed on the cell surface of ANLL cells. Our studies (16 Ref.a) have demonstrated rapid modulation of these sites after antibody binding.

Several antigens are currently used to diagnose ANLL by flow cytometry. Among these, CD33 antibodies, MY9 (5 Ref.a), and L4F3 or LIB2 (4 Ref.a), appear to be most widely and most specifically distributed on ANLL. M195 antigen was concordantly expressed with MY9 on 83% of cases. Moreover, although neither antigen was expressed on 100% of ANLL, the combination of both M195 and MY9 could be used to diagnose ANLL with 98% specificity if both were expressed on a leukemia sample. We are currently using this combination to aid in the diagnosis of acute leukemias at Memorial Hospital.

The close coexpression of M195 and MY9 suggested that M195 might bind to the CD33 protein target [p67] (20 Ref.a). Efforts to identify the M195 target have been unsuccessful (16 Ref.a). Blocking experiments shown here demonstrated probable identity of the M195 target with the CD33 protein. Moreover, binding of M195 and CD33 DNA transfectants was shown. Despite these data, since flow cytometry data showed nonidentical concordance with MY9, it is likely that M195 does not bind to the same CD33 epitope as MY9 or L4F3.

Although M195 antigen was found on a greater percentage of ANLL samples of the FAB classifications M2, M3, and M4 than on other types, the presence of M195 binding could not be used to predict morphology or vice versa. Other studies comparing immunophenotype with morphologic phenotype have come to similar conclusions since there was considerable overlap of markers into each type of ANLL (23–25 Ref.a). Some discrimination of monocytic from myeloid ANLL has been shown (22,26 Ref.a), however.

The CD33 antigen is expressed on early myelomonocytic progenitors cells (4,5 Ref.a), but not on the ultimate progenitors (17 Ref.a). This restriction has allowed selective purging of ANLL cells from bone marrow while still permitting regrowth of normal cells in selective cases (18 Ref.a)(Lemoli R. M., Gulati S. C., Scheinberg D. A., Gasparetto C., Moore M. A. S., Clarkson B. D., Gee T., Autologous Bone Marrow Transplantation in Acute Myelogenous Leukemia (AML): In Vitro Treatment with Myeloid-Specific Monolconal Antibodies (MoAbs) and Drugs in Combination. Blood 74(7):suppl,p280a abstract) (1989) see Experiment 5). M195, as expected, was expressed on CFU-GM and to a lesser extent on BFU-E. Since, like MY9 and L4F3, M195 readily kills cells with rabbit complement, it is useful as a purging agent in ANLL. Radioimmunoassays with M195 on highly purified early blasts did not detect significant antigen expression. Because the radioimmunoassay could miss M195 expression on small subpopulations within this group of cells, long-term marrow cultures were done (Lemoli R. M., Gulati S. C., Scheinberg D. A., Gasparetto C., Moore M. A. S., Clarkson B. D., Gee T., Autologous Bone Marrow Transplantation in Acute Myelogenous Leukemia (AML): In Vitro Treatment with Myeloid-Specific Monoclonal Antibodies (MoAbs) and Drugs in Combination. Blood 74(7):suppl,p280a abstract) (1989) see Experiment 5) to help further define and confirm this finding. Based on the data here and in Experiment 1 (16 Ref.a) the distribution of the M195 antigen among hematopoietic differentiation appears similar to that described for other CD33 antigens (4,5 Ref.a). This includes early committed myeloid progenitors, but not the earliest colony forming cells (Lemoli R. M., Gulati S. C., Scheinberg D. A., Gasparetto C., Moore M. A. S., Clarkson B. D., Gee T., Autologous Bone Marrow Transplantation in Acute Myelogenous Leukemia (AML): In Vitro Treatment with Myeloid-Specific Monoclonal Antibodies (MoAbs) and Drugs in Combination. Blood 74(7):supp1,p280a abstract) (1989) see Experiment 5) (17,18 Ref.a).

The M195 antigen is not expressed on adult human tissues. Therefore, in addition to its use as a diagnostic marker of ANLL and as a purging agent, M195 can potentially be used as a therapeutic agent in vivo. Since the antibody does not have in vitro cytotoxic effects alone or in the presence of human serum as a complement source, it is not likely to cause lysis of ANLL cells. However, upon binding of mAb M195, the antibody is rapidly internalized (Divgi, Internalization of Radionuclides (Experiment 3)), and thus the application of mAb M195 as a carrier of toxins or isotopes to ANLL cells in vivo is feasible.

EXPERIMENT 3

In this experiment, we focus on the impact of modulation and mAb internalization and release on the delivery of radionuclide into tumor cells. We investigated the behavior of two prototype radionuclides, radioiodine and radioindium, when attached to mAbs currently under evaluation at Memorial Sloan-Kettering Cancer Center in Phase I clinical trials.

Iodine-125 serves as a prototype for all halides such as 77Br, $^{123}$I, $^{131}$I, $^{211}$A, and $^{124}$I. $^{111}$In serves as a prototype for all radiometals such as $^{211}$Bi, $^{25}$Tb, $^{90}$Y, $^{186}$Rh, and $^{188}$Rh. The mAbs modulate subsequent to interaction with antigen. Mab M195 is reactive with a 67 KD cell-surface glycoprotein found on most myeloid leukemia cells (24,25 Ref.c), and is reactive with the Epstein Barr Virus (EBV) receptor, a 140 KD glycoprotein surface receptor expressed on most B-cell lymphoma cells and chronic lymphocytic leukemia (26,27 Ref.c). In addition, we explored the behavior of a proteolytic digestion fragment of the antibody.

MATERIALS AND METHODS

Cells:

HL60, a myeloid leukemia cell line, were maintained in log phase growth in RPMI 1640 supplemented with 10% FCS and 10% 1-glutamine at 37° C. in 5% carbon dioxide. Cells were utilized only if the viability (as estimated by trypan blue exclusion) was 95% or greater.

Antibodies:

M195 is an IgG2a monoclonal antibody (mAb) reactive with a 67 KD cell-surface glycoprotein found on most myeloid leukemia cells (24,25 Ref.c). The antibody was purified from mouse ascites fluid using Protein A affinity chromatography. M195 F(ab')$_2$ was prepared by pepsin digestion of the intact immunoglobulin; OKB7 Fab was prepared by papain digestion.

Radioiodination:

Intact antibodies and their fragments were labeled with iodine-125 by the chloramine-T method (28 Ref.c). 100 ug of antibody was incubated with 2 mCi of $^{125}$I and 20 uL of a freshly prepared solution of chloramine-T at a concentration of 2 mg/mL in 0.2M phosphate at pH 7.4 for 1 minute at room temperature. The reaction was quenched with 20 uL of a freshly prepared solution of sodium metabisulfite at 20 mg/mL and incubated for 5 minutes. The radiolabeled antibody was purified by exclusion chromatography (Sephadex G25, Pharmacia Inc., Piscataway, N.J.). Further purification of the mAb from free radionuclide was effected by dialyzing the radiolabeled mAb at 4° in phosphate buffered saline (PBS), pH 7.4.

Immunoreactivity of the labeled antibody (that proportion of antibody molecules in a preparation which were capable of binding to antigen) was determined by modifications of previously described methods (28,29 Ref.c) as follows: $10^7$ cells of at least 95% viability at 4° C. were incubated with 5 ng of the radiolabeled antibody for 60 minutes. The percent bound was estimated; the supernatant obtained after centrifugation was transferred to a similar set of cells and the process repeated until binding was no greater than with a control cell line. Immunoreactivity was not less than 65% for M195.

$^{111}$Indium Labeling:

The intact immunoglobulins were conjugated with diethylene triamine pentaacetic acid (DTPA) as described (31 Ref.c). After conjugation, each antibody was labeled with $^{111}$In by incubation with $^{111}$In at a pH of 3.0 for 60 minutes at room temperature. The reaction was quenched by increasing the pH to greater than 6.5 using 0.2M metal-free phosphate buffer (pH 7.4). The radiolabeled mAb was purified using a Chelex metal-binding column followed by size exclusion chromatography. Further removal of free $^{111}$In from mAb was accomplished by dialyzing the radiolabeled mAb at 4° in metal-free PBS, pH 7.4. Immunoreactivity of the labeled antibody was comparable to that of the respective radioiodinated antibody.

Radionuclide Internalization 5 million viable cells in 5 mL media were incubated with 5 ug radiolabled antibody, at either 4° or 37°. Immediately after addition of the radiolabeled mAb (or fragment) and at several times afterward, 200 uL aliquots from each batch of cells were taken and washed three times. 1.5 mL glycine/sodium chloride (50 mM glycine/HCl, 150 mM sodium chloride, pH 2.8) was added to each pellet. "Total" cell-associated radioactivity was determined in a gamma counter after mixing. The cells were then centrifuged, the supernatant aspirated, and the cell pellet re-counted to determine "internalized" radioactivity. "Cell surface" radioactivity was calculated as the difference between total and internalized radio-activity. This general method has been used to study internalization of other cell surface receptors(20–22 Ref.c). We have confirmed that this direct method measures true losses of antibody from the surface by indirect methods (indirect radioimmunoassay and complement fixation) as well. The percent radioiodine bound to protein in the supernatant was estimated by TCA precipitation of the supernatant; it was never less than 95%. Similarly, protein-bound radioindium was estimated in aliquots of selected supernatants by thin layer chromatography and was always greater than 90%.

Radionuclide Release:

5 million viable cells in 5 mL media were incubated with 5 ug radiolabeled mAb or fragment at 4° for 60 minutes. The incubated cells were then washed two times in media and resuspended to the same volume. Baseline total and internalized radioactivity was determined as described above. Immediately after washing, the washed cells were separated into two parts and kept at either 4° or 37°. Total cell-associated radioactivity and internalized radioactivity were then determined over time as described above.

RESULTS

All experiments were done 2–6 times and all time points were done in duplicate. The mean of two determinations was recorded. Maximal binding of M195 was about 10,000 sites per cell; for OKB7, about 100,000 sites per cell.

Internalization experiments were designed to study changes in the kinetics of binding and cell-associated radioactivity in the presence of excess ambient antibody, a condition which might occur during an antibody infusion in patients. The release experiments were designed to study the same phenomena, after a period of binding, in the absence of ambient antibody which might mimic conditions in vivo following termination of mAb infusion.

125I-M195 Internalization and Release: (FIGS. 8A-D)

At 4°, there were initial increases in the total amount of cell-associated radioactivity, with minimal internalization of $^{125}$I (FIG. 1A). Bound $^{125}$I increased about 4-fold and plateaued by 2 hours, suggesting completion of binding and saturation of sites within this time period. At 37°, there was a similar increase in total cell-associated radioactivity over time as at 4°. In contrast, there was a significant greater increase in the amount of internalized radioactivity over time, with most of the increase being noted in the first two hours. After two hours, the internalized radioactivity stabilized at about a 12-fold higher level than at time 0.

The release experiments for M195 IgG (FIGS. 9C-D) showed no significant change in cell-associated radioactivity over time at 4°; the amount of radioactivity in the surface and within the cell did not change over time. At 37°, there was an initial rapid clearance of about 40% of the cell-associated radioactivity. The radioactivity that cleared appeared to be accounted for by net loss from the cell surface. Whether this was direct or via an internalization step cannot be determined from these data. There was an increase in internalized radioactivity with time. Clearance of radioactivity from the cell surface occurred during the first hour, after which the total amount of cell-associated radioactivity stayed constant while the amount of internalized radioactivity increased to plateau toward the end of the experiment.

Figure 8B:
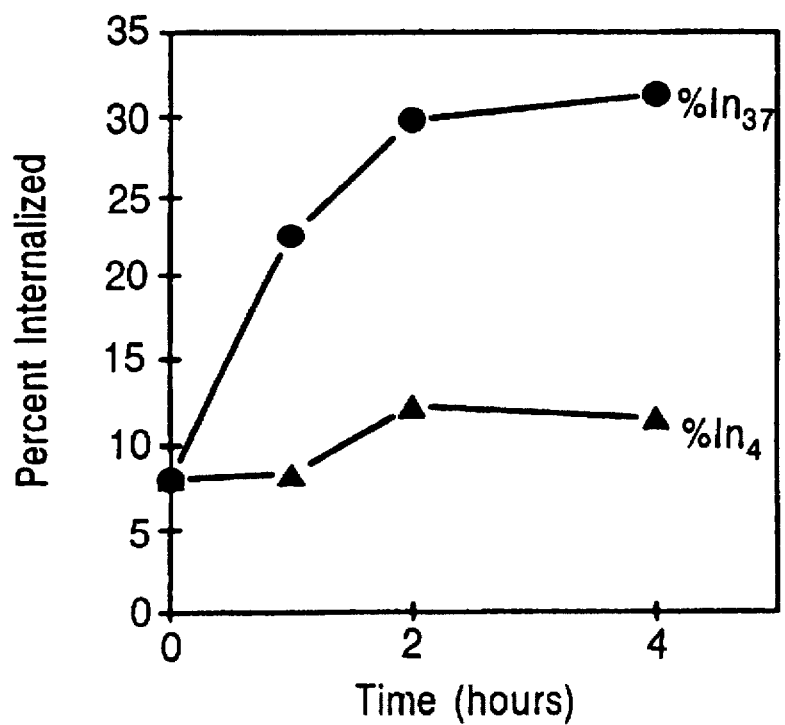
Figure 8C:
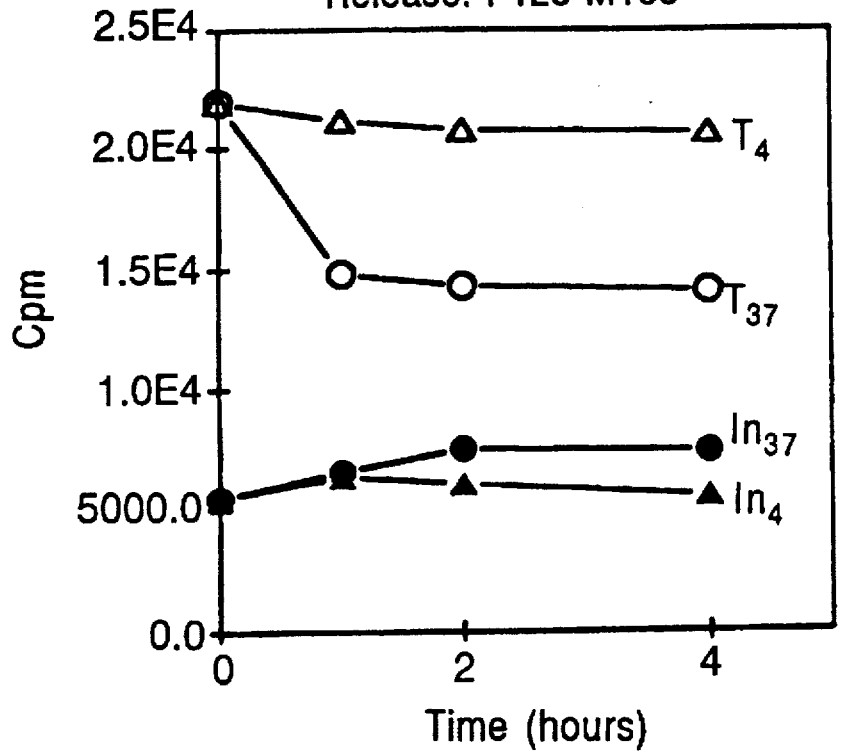
Figure 8D:
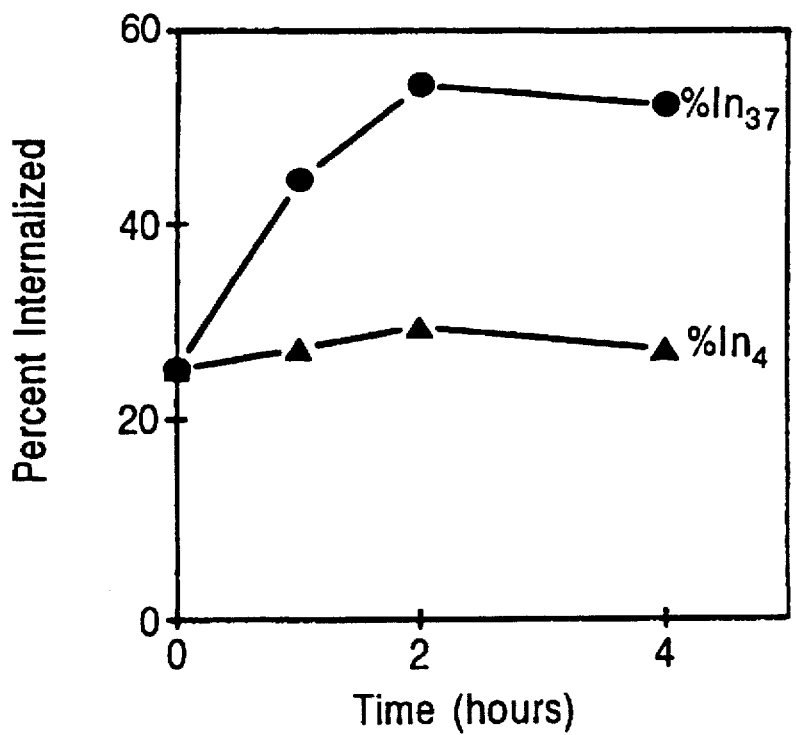

The present of cell-associated radioactivity that was internalized was constant for cells at 4° (FIGS. 8B, D). At 37° the percent of internalized radioactivity approached 35% of total cell-associated radioactivity in the presence of excess antibody, and up to 60% in the absence of ambient antibody.

In the presence of surrounding antibody there appeared to be no net loss of cell-associated radioactivity, with increases in the amount within the cell contributing to the increase in percent radioactivity internalized. In contrast, in the absence of ambient antibody (FIGS. 8C, D), there was a net loss of total cell-associated radioactivity manifest as a transfer of radioactivity from the cell surface to both the surrounding media and to the cell interior.

This may have occurred either because of internalization followed by release or by an independent direct release of surface-bound radioactivity into the media. This net loss translated to an increase in the percent radioactivity internalized greater than that apparent solely from the increase in internalized radioactive counts. The net result Was that after 2 hours, more than half the radioactivity associated with the HL60 cells was intracellular.

$^{111}$In-M195 Internalization and Release: (FIGS. 9A-D)

Figure 9A:
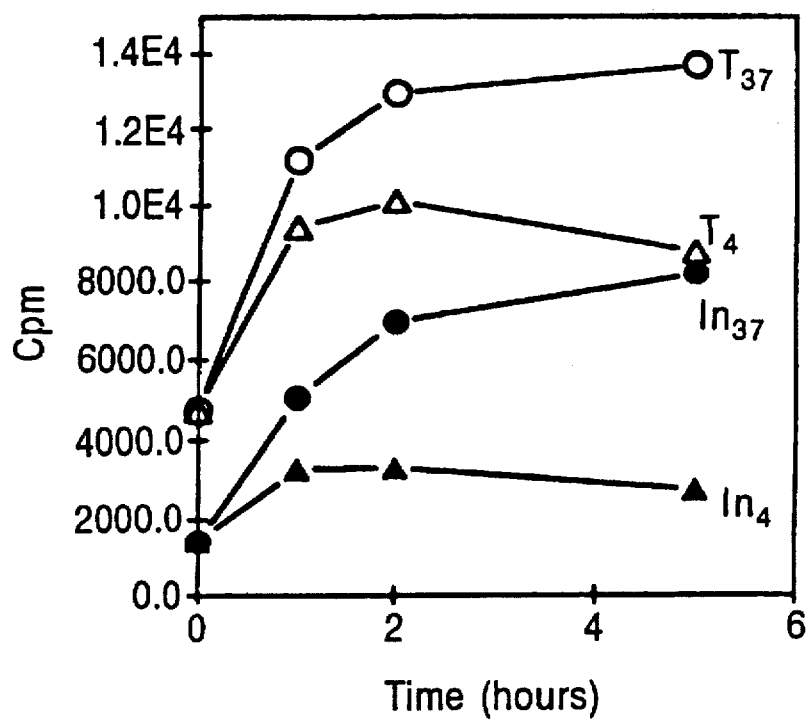
Figure 9B:
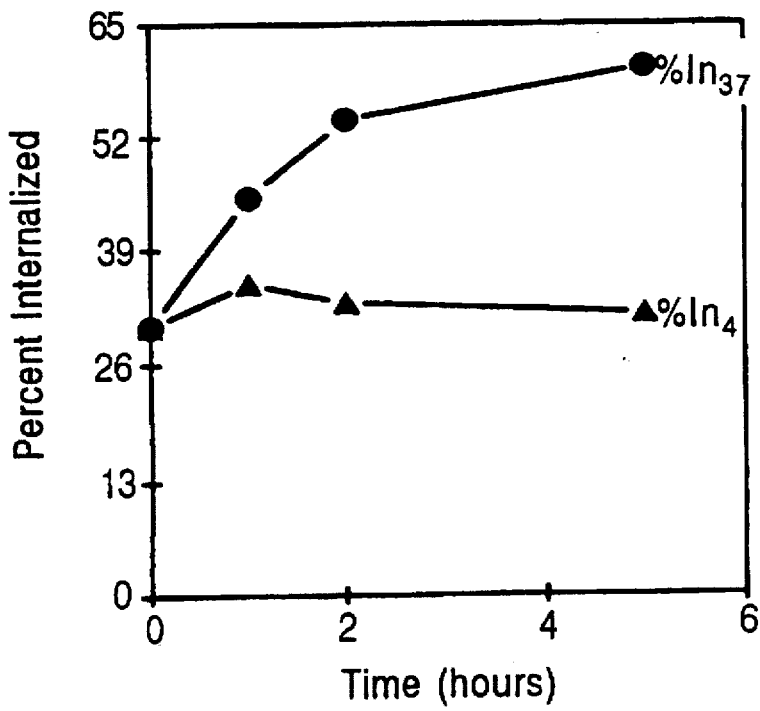
Figure 9C:
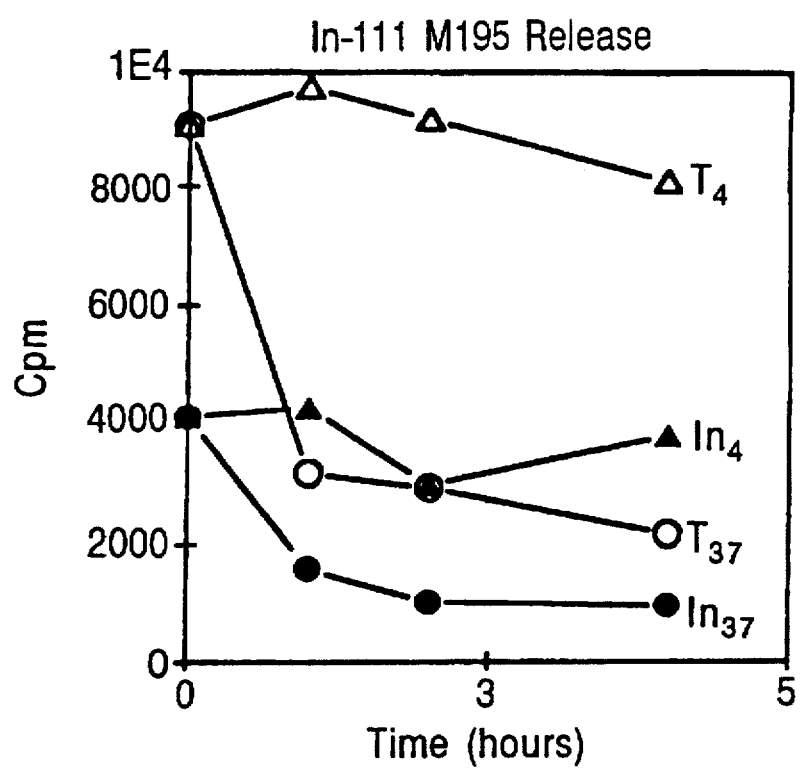
Figure 9D:
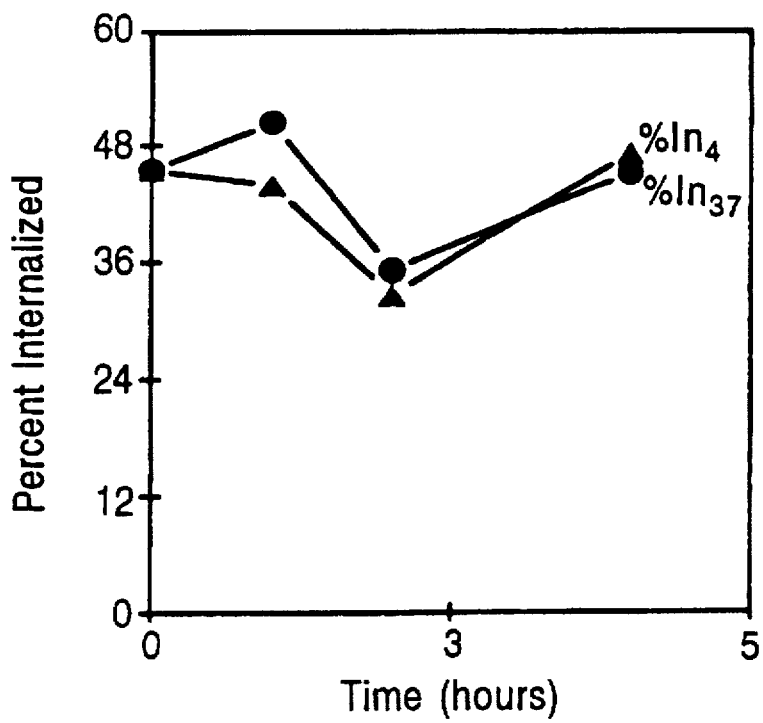
Figure 10A:
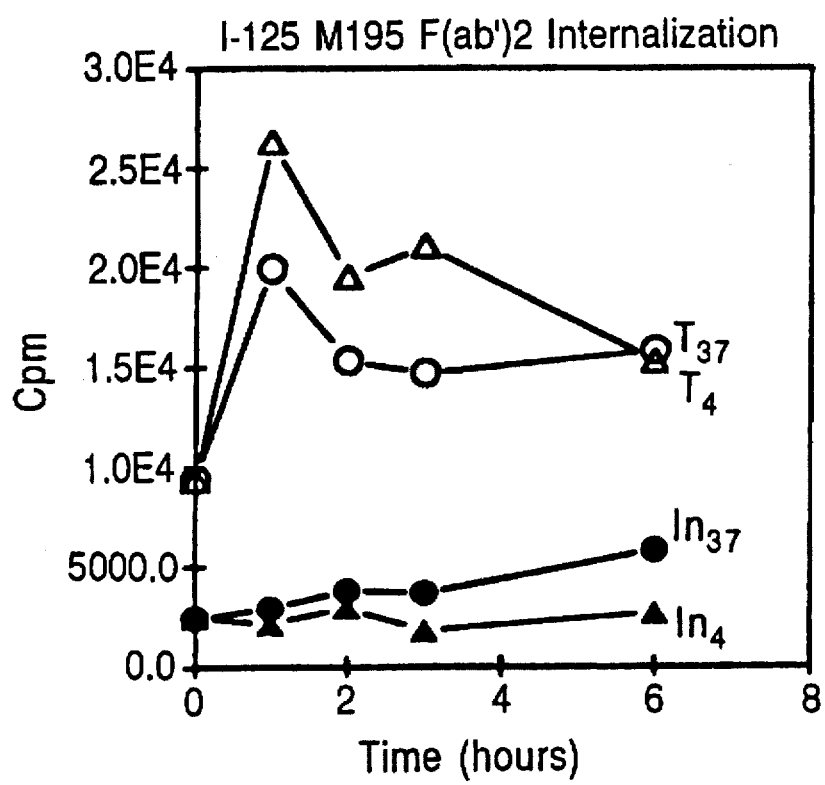
Figure 10B:
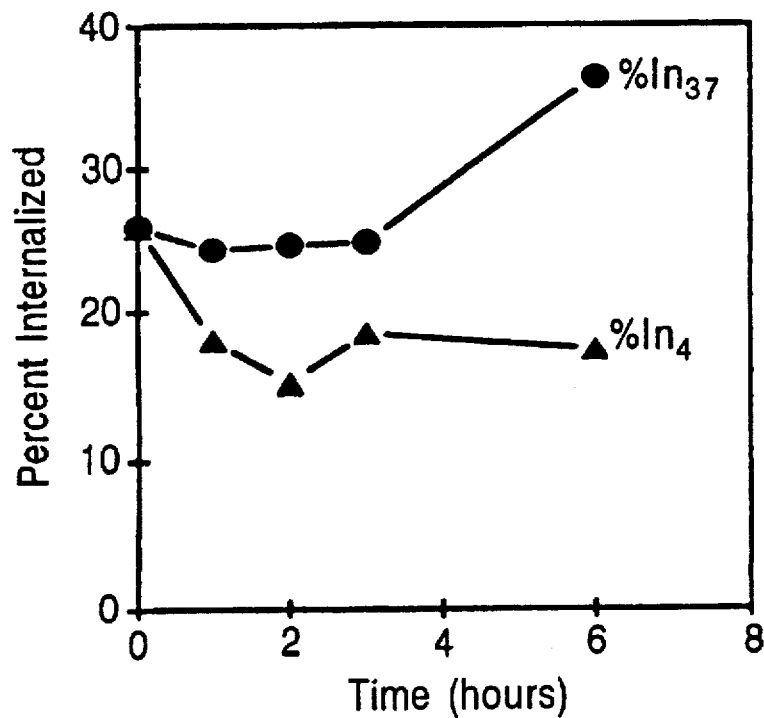
Figure 10C:
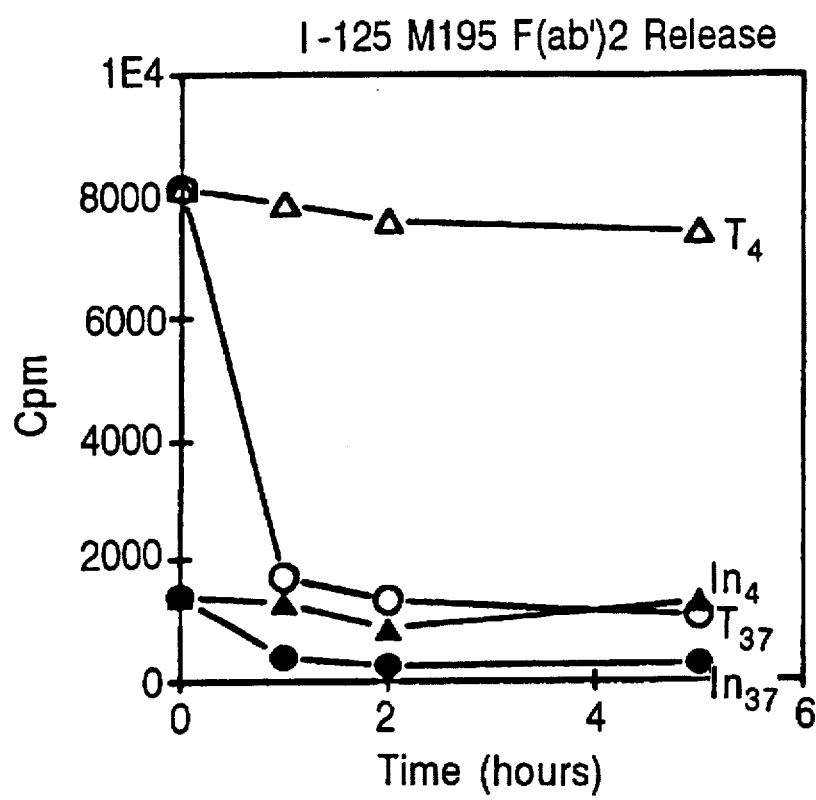
Figure 10D:
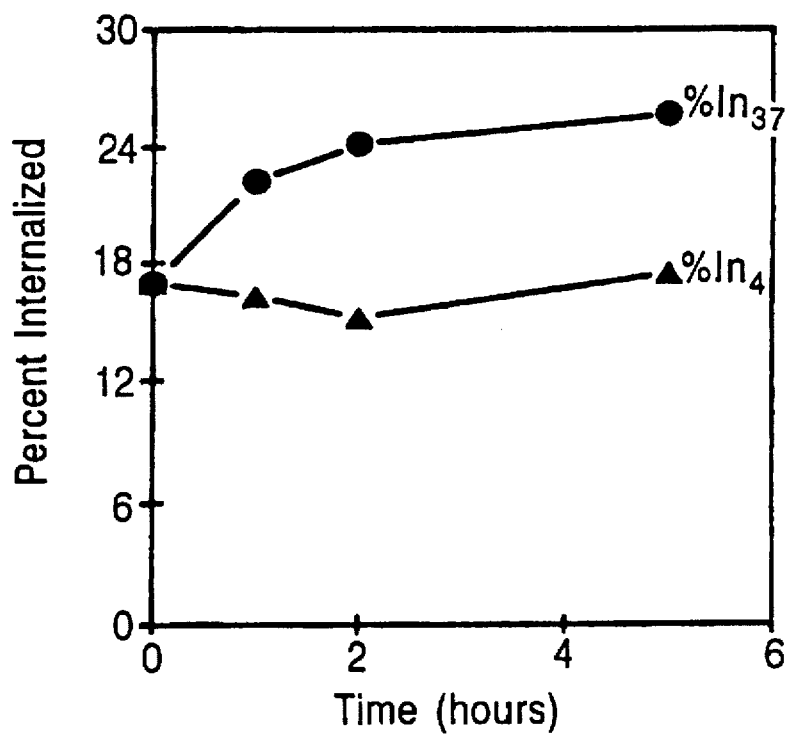

Additional experiments were conducted as above, using $^{111}$In-M195 (FIGS. 9A, B). Large increases in internalized radioactivity occurred over time at 37° as compared to 4° (FIG. 9A). Internalization of $^{111}$In as a percentage was consistently higher than with $^{125}$I, increasing with time, not showing a plateau out to 4 hours, to reach approximately 70% in some experiments. This may be due in part to a greater loss (60%) of total $^{111}$In at 37° (FIG. 9C), perhaps by release of chelated $^{111}$In from surface-bound IgG. In this as well as the $^{111}$In-OKB7 experiments, the background percent internalization was considerably greater than observed with $^{125}$I-labeled antibody, perhaps due to transchelation of $^{111}$In to cellular protein.

In summary, at 4°, when cells would be expected to be metabolically quiescent, there were no major changes in cell-associated radioactivity over time, whether on or in the cell and whether or not there was surrounding antibody present. In contrast, cell-associated radioactivity changed dramatically over time at 37° when the cells are metabolically active.

$^{125}$I-M195 F(ab')$_2$ Internalization and Release: (FIGS. 10A-D)

In contrast to the findings observed with the intact Ig, with the F(ab')$_2$ the early increase in total cell-associated radioactivity decreased moderately with time. The internalized radioactivity, however, increased gradually with time at 37° while staying relatively constant at 4°. Background (time 0) radioactivity was consistently higher with the F(ab')$_2$. The increase in internalized radioactivity was not as great over time with the fragment as with the intact Ig (26% to 37% with the fragment compared to 6% to 32% with the Ig).

In the absence of ambient antibody, there was rapid decrease in the total cell-associated radioactivity with time at 37%; this was accompanied by a significant, albeit small, decrease in the total amount of radioactivity within the cell; the percent internalized over time at 37° therefore did not increase as much as with the intact Ig.

Because of differences in specific activity of the labeled Ig and fragments and differences in counting efficiency of the two radionuclides among the different sets of experiments, all changes over time in an individual experiment were related to conditions at time 0 to enable us to compare experiments (Table I). Radioactive counts at time (n) were expressed as a percentage of those at time 0 (Cpm$_{(t=n)}$/Cpm$_{(t=0)}$33 100). Several conclusions became apparent.

With M195 Ig, an antibody that rapidly internalizes in the presence of ambient excess antibody (the internalization experiments), there was no significant difference between the changes in amounts of radioindium internalized as compared to the changes in amounts of radioiodine internalized (1130% vs. 1300%). In contrast, the percent losses of radioiodine from the cell in the absence of ambient antibody (the release experiments) were considerably less than the losses in amounts of $^{111}$In. The relative increase in percent internalized was primarily a result of greater loss of cell-associated radioactivity. Radioiodine attached to the fragment cleared at an even faster rate than that of $^{111}$In.

DISCUSSION

As the number of clinical trials employing radioactively tagged monoclonal antibodies for diagnostic imaging or radioimmunotherapy increases, the need for an understanding of the kinetics of antibody binding and internalization of nuclide become increasingly important. Significant differences in binding of $^{111}$In labeled antibody compared to radioiodinated antibody have been demonstrated in vitro and in vivo (14-17 Ref.c). The experiments here attempt to describe some of these differences at the cellular level. We show that internalization of radionuclide into target tumor cells is dependent upon the choice of radionuclide, the antigen-antibody system concerned, and the nature of the antibody used, either intact immunoglobulin or fragment.

Recently, Press et al. (20 Ref.c) compared the binding and degradation characteristics of a panel of radioiodinated antibodies reacting against B-cell tumors. As we have also confirmed here, distinct differences in internalization kinetics were found between mAbs. In addition, we also studied the behavior of intact and fragmented mAbs when labeled with two different prototype radionuclides, $^{125}$I and $^{111}$In. Significant detachment of radionuclide from antibody was not seen at the early time points we studied. This is similar to results observed by Press and associates. Because steady states were reached within 2-4 hours, we did not examine behavior at late time points.

In the presence of excess surrounding antibody, M195 Ig was rapidly internalized by the cell subsequent to interaction with the target antigen. For both nuclides, there were no differences in binding kinetics (Table I). With the F(ab')$_2$, there were minimal changes in total and internalized radioactivity. After ambient M195 Ig or F(ab')$_2$ had been washed away, there was greater loss of $^{111}$In-labeled compared to $^{125}$I-labeled Ig, and much greater internalization with the Ig than with the F(ab')$_2$). We do not know if these differences reflect the minor difference in avidity (3×10$^9$ L/M for the intact Ig compared to 10$^9$ L/M for the F(ab')$_2$).

Internalization and release kinetics of radionuclide labeled to a mAb that is internalized rapidly were not dependent on the nature of the radionuclide used. Radionuclide attached to the intact M195 Ig showed far greater internalization than when attached to its fragment. Studies with the Fab fragment suggested that lack of modulation and internalization may be more apparent in the absence of excess surrounding antibody.

In a clinical trial using M195 (whether diagnostic or therapeutic), intact M195 Ig might be preferable to the fragment, as a significantly greater amount of radioactivity would then be internalized. The $K_D$ of the F(ab')$_2$ is 10$^9$ L/M compared to a $K_D$ of 3×10$^9$ L/M for the intact immunoglobulin; we do not know if the difference in internalization was caused by this small difference in dissociation constants or some other unknown change in antibody binding consequent to creation of the F(ab')$_2$. Although there was greater clearance of $^{111}$In from the cell in the absence of ambient mAb, there was also a significantly greater amount internalized. Since in the absence of ambient antibody there is greater loss of cell-associated radioactivity when $^{111}$In is the radionuclide used, the ideal radiolabel to be used might either be a suitable isotope of iodine or a radiometal depending upon the physical half-life of the radionuclide and the biological half-life of the antibody in the host.

Although the kinetics of binding, internalization, and release are important, the choice of nuclide for clinical therapy trials would also be affected by the physical half-life, emission characteristics, and cytotoxic potential of the radionuclide under consideration, as well as by labeling characteristics and serum clearance. Dehalogenation of iodine-labeled antibody has been described (17 Ref.c), but current methods of chelation also result in detachment of radiometal from antibody in vivo (17 Ref.c) and human trials have not been uniformly successful to date. Progress in new chelation chemistry may solve these problems (32 Ref.c). Moreover, if radionuclides that decay by electron capture are more cytotoxic when internalized into the cell than those that undergo beta-minus decay, then $^{125}$I and $^{123}$I would be candidate radionuclides for therapeutic purposes. A recent report by Woo et al. (13 Ref.c) has shown significant cytotoxicity with $^{125}$I-labeled antibody compared to unlabeled antibody, postulated to be due to cytotoxicity of intranuclear $^{125}$I. We have also seen significantly enhanced growth suppression of $^{125}$I-labeled anti-epidermal growth factor receptor antibody compared to $^{131}$I-labeled or unlabeled antibody in cells expressing increased quantities of the receptor. We are now studying the cytotoxicity of iodine labeled M195 in vitro.

In summary, the choice of both the radionuclide and the antibody form has great impact on the kinetics of radionuclide internalization and retention in target cells and therefore, may be of crucial importance in the design of clinical trials utilizing radiolabeled antibodies. Preclinical studies of cell binding and internalization such as those described here may help suggest an optimal approach for imaging or therapy.

EXPERIMENT 4

(ASCO, Scheinberg May, 1990, Submitted for Publication)

A Phase I Trial of Monoclonal Antibody M195 (Anti-CD33) in AML: Pharmacology, Toxicity, Radiolocalization Mouse monoclonal antibody (mAb) M195 reacts with myeloid leukemia cells, early myeloid progenitor cells, some mature monocytes, but with no other adult cells or tissues. A phase I trial using escalating amounts of M195 in 4 daily doses was initiated in patients with relapsed or refractory AML (3 patients per dose level). First doses were trace labeled with iodine-131. After 7 patients (3 at 1 mg/m$^2$, 4 at 5 mg/m$^2$), the following has been observed: Rapid, specific targeting to leukemia cells in both blood and bone marrow was observed in all patients within 1 hour as documented by serial blood sampling and bone marrow biopsies and aspirates. Whole body gamma camera images showed uptake in all bone marrow areas and spleen. Efficient targeting occurred in hypoplastic, pancytopenic patients as well as in patients with an estimated leukemic burden in excess of 10$^{12}$ cells, even at the 1 mg dose level. 10$^3$-10$^4$ antibodies were delivered per cell within 1 hour with persistence in the bone marrow for several days. The first patient had mild transient generalized pruritis during infusions. One patient developed persistent bone marrow pain after the third dose of 5 mg/m$^2$. Since M195 is an IgG2A which exhibits no cytotoxicity in vitro using human effector cells or complement, no therapeutic responses were expected or observed yet. Because M195 is rapidly internalized into cells, these data show that rapid, specific delivery of radionuclides, toxins or other immunoconjugates into marrow cells will be feasible with M195.

Monoclonal Antibody Therapy. Several pilot trials have been conducted using unlabeled hematopoietic neoplasms (reviewed in Rosen S T, Zimmer A M, et al. J Clin Oncol 5:562–573, 1987). Toxicity was tolerable and responses were seen, but they were almost always transient. None of the original trials used antibodies with intrinsic cytotoxic capability and responses were probably abrogated by lack of effector functions, antigen modulation and human antimouse Ig responses. More recent trials (Ball E D, Berneri G M, Cornwell G G, et al. Blood 62:1203–12110, 1983; Tanimoto M, Scheinberg D A, Cordon-Cardo C, et al. Leukemia 3:339–348, 1989) using radioisotope-labeled monoclonal antibodies have achieved high major response rates. These trials utilized large doses of Iodine-$^{131}$-labeled monoclonal antibodies to T-cell lymphomas, chronic lymphocytic leukemias, and nodular lymphomas. The major adverse reactions were hematologic, related to the high doses of radiation. In the trial with T cell lymphomas and CLL, remissions were short lived. It is too soon to know the long term outcome in the nodular lymphoma trials. No study of monoclonal antibodies has been completed with patients with ANLL, but three patients were treated (Scheinberg D A, Tanimoto M, McKenzie S, et al. Leukemia 3:440–445, 1989) with minimal responses and toxicity with a cocktail of antibodies. These antibodies recognized different antigen targets than M195 recognizes. Despite large doses of antibody (up to several hundred mg), blast counts were suppressed only transiently in the three patients. All three patients had fever and one had urticaria due to the infusions, but the antibodies were not highly purified. We have seen no toxicity here in 26 patients with B-NHL, Hodgkins Disease, and T-NHL, treated with monoclonal antibodies OKB7 or R24, at doses ranging from 0.1 to 100 mg.

M195. Mouse monoclonal antibody M195 is an IgG2a developed at Sloan-Kettering Institute (Tanimoto M, Scheinberg D A, Cordon-Cardo C, et al. Leukemia 3:339–348, 1989. Scheinberg D A, Tanimoto M, McKenzie S, et al. Leukemia 3:440–445, 1989.) which reacts with 60–70% of samples of blasts from patients with ANLL. M195 also binds to early myeloid cells (CFU-GM) and some monocytes but not to the earliest myeloid progenitors. The target antigen is not expressed on any other hematopoietic or non-hematopoietic tissue. Antibodies to a related antigen on the same protein (CD33), My9 and L4F3, are currently being used to purge bone marrow of ANLL before autologous transfusion (Bernstein I D, Singer J W, Andrews R G, et al. J Clin Invest 79:1153–1159, (1987); Griffin J D, Linch D, Sabbath K, et al. Leukemia Res 8:521–534, 1984.). M195 is rapidly internalized into cells after binding and this effect can enhance delivery of radiometals, radioiodine or conjugated toxins into cells (Divgi C R, Minniti J G, Old L J, Scheinberg D A Amer Assoc Cancer Res 30: Abs #1606, 1989). M195 is able to kill leukemia cells with rabbit or guinea pig complement, but not by use of human complement or human antibody-dependent cellular cytotoxicity in vitro. Activation of these mediators in vitro has correlated with these effects in vivo (Houghton A N, Mintzer D, Cordon-Cardo C, et al. Proc Natl Acad Sci USA 82:1242–1246, (1985)), but it is not known if the lack of in vitro effects will predict lack of in vivo effects. Because M195 also reacts with early myeloid cells, normal marrow progenitors may be affected also.

Studies of M195 in Humans. In order to determine the toxicity, biodistribution, pharmacology and dosimetry of radiolabeled M195 in humans, a pilot trial involving 9 patients with ANLL was initiated under IRB approval (#89-113A(1)) at Memorial Hospital. The trial involves a dose escalation of M195 (1, 5, 25 mg/m² per dose) with 4 doses of antibody given over 1 week. In this trial the first (and sometimes second) doses of antibody were trace-labeled with iodine-131 to allow whole body imaging for biodistribution and half-life calculations, and accurate pharmacology and dosimetry studies based on repeated blood and marrow samplings.

The following data were derived from the first three patients treated:

| Feature Studied | Patient #1 | Patient #2 | Patient #3 |
|---|---|---|---|
| Age/Sex/Dx | 25 y.o. male-AML, refractory | 20 y.o. woman-AML, relapsed | 24 y.o. male AML, relapsed |
| Prior Therapy | Multiple chemo-therapies | Multiple chemo-therapies allogeneic BM transplant | Multiple chemo-therapies |

-continued

| Feature Studied | Patient #1 | Patient #2 | Patient #3 |
|---|---|---|---|
| Circulating blasts | 30,00/mm² | 100/mm² | 10/mm² |
| BM Status | Packed | Hypoplastic | Partially Hypoplastic |
| Clinical Status | Severely ill; multiple infections; bleeding | Stable | Stable |
| Doses Toxicity | 1.5 mg x4 Transient itching during infusions | 1.5 mg x4 None | 2.0 mg x4 None |
| T ½ Blood Images | <1 day All areas of leukemia including predominantly BM; no blood pool (18–89 hours) | >4 days Blood Pool | 3 days Marrow; No Blood Pool |
| M195 IgG per leukemia dell (Estimated) | 1200 | 4000 | 1400 |

We concluded that there was rapid and specific uptake of M195 onto target cells and that sufficient numbers of M195 were bound to each cell to allow a therapeutic dose of radioisotope, even at this first dose level (1 mg/m²), at wide variations of tumor burden (patient 1: >1 trillion cells; patient 2: <100 billion cells).

Microdosimetry of 1–123. The localization of the M195 mAb on the surface of the leukemia cell and its subsequent incorporation into the cytoplasm presents an opportunity to select a radionuclide with properties that exploit this situation. Electron emissions that have a range on the order of a cell diameter (10–20 microns) deposit a large fraction of their energy within the cell (Kassis A I, Adelstein S J, Haycock C, Sastry K S R. Radiation Research 84:407–425 (1980)). Electron capture (EC) is a mode of decay that gives rise to a large percentage of such low energy emissions. The isotopes of iodine that decay by EC include I-125 (T–½=60 d) and I-123 (T–½=14 h), the latter being advantageous in terms of a physical half-life matching the expected biological clearance times. From a microdosimetric point of view, in cells on the order of 10–12µ in diameter, it is more effective than I-131. Another advantage of I-123 is relatively low marrow dose per millicurie from the 127 key (13.7%) conversion electron. The isotope also has superior imaging characteristics for confirming dose distribution as well as the dosimetry.

Assuming that at most half of the labeled dose is concentrated uniformly in the marrow, and T–effective=T–physical, the dose to the marrow cavity is 0.27 rad/mCi administered. Thus, only 27 rad/100 mCi would be administered. Examination of radiation exposure of nursing staff, radiation dose to other organs within the patient and the cost of the radionuclide, activities of about 200 mCi would appear to be safe and practical. However, with the above assumptions, 200 mCi would be sufficient to kill only about $10^{10}$ leukemia cells. This is based on the following arguments:

200 mCi represents $5.4 \times 10^{14}$ atoms of I-123. Based on presented and published work of Howell, Sastry, Rao et al (Howell, private communication) it appears that approximately 1 MeV of energy must be deposited in the nucleus on average from such electron capture nuclides to achieve cell kill. This corresponds to approximately 2000 disintegrations from atoms in the cytoplasm (Kassis A I, Adelstein S J, Haycock C, Sastry K S R. Radiation Research 84:407–425 (1980)), or in this case, also atoms on the cell surface since the radius of the cell may only be about 1–2 microns greater than that of the nucleus. Based on observed biological clearance in initial patient studies here and the known physical half life (14 hours) of I-123 a reasonable assumption is that about half the atoms taken up by the cell will decay while on or in the cell. (There are approximately 10,000 surface binding sites per cell. Labelling carried out at 1 atom of I-123 per 8 antibodies will result in 200 mCi of I-123 on about 1.0 mg of antibody.) Ideally 200 mCi ($5.4 \times 10^{14}$ atoms) at 5000 atoms of I-123 disintegrating per cell should kill $1.1 \times 10^{11}$ cells. However, since the targeting efficiency is only about 20–30%, 200 mCi will theoretically only kill about $3 \times 10^{10}$ cells at most.

Pharmacologic limits and need for cytoreduction. Based on the first phase I study of M195 and on achievable and practical levels of $^{123}$I-M195 specific activities, described in 2.5 (determined by physical properties of both antibody and isotope, data on antigen expression and antibody immunoreactivity, radiation safety concerns and costs of isotope), it does not seem practical to expect at this time that the $^{123}$I-M195 will effectively target to 12 logs of cells (typical tumor burden). Therefore, we will cytoreduce the patients 3 days before M195 therapy with a small dose of Ara-C calculated to kill 1–2 logs of leukemia cells and leave $10^{10}$–$10^{11}$ cells at day 4 when $^{123}$I-M195 begins. This dose of Ara-C will be in no way therapeutic and will therefore still enable us to determine the therapeutic effects of M195. The toxicity of this chemotherapy should also be minimal.

Radiometal Chelate-Conjugated Antibodies. Radiometals have been attached to monoclonal antibodies via bifunctional chelates for diagnostic imaging and therapy. We have proposed the use of alpha particle emitting nuclides, Lead 212 or Bismuth 212 as the optimal radiotherapeutic nuclides for use in killing leukemia cells based on emission characteristics and pharmacology studies in animals (Brechbiel M W, Gansow O A, Atcher R W, et al. Inorg Chem 25:2772–2781, 1986; Kumar K, Magerstadt M, Gansow O A J Chem Soc Chem Commun, 3:145–146 (1989)). Rotationally hindered benzyl derivates of DTPA and planar cage structures such as DOTA have been developed recently to chelate bismuth (Gansow O A, Atcher R W, Link D C, Friedman A M, Sever R H, Anderson W, Scheinberg D A, Strand M In: F F Knapp and J A Butler (eds) Radionuclide Generators, Vol 241, pp 215–230. Washington, DC. ACS. (1984)). These chelands have been conjugated to M195 without loss of immunoreactivity and the chelated Bismuth 212 can be made without loss of binding activity. These chelates are able to kill leukemia cells in model systems in vitro. Animals models of other Bismuth conjugated antibodies show no loss of bismuth to non-target organs.

FIG. 11: Schematic diagram of the distribution of the M195 antigen in human tissues. The antigen is not known to be present on any adult non-hematopoietic tissues, so they are not shown. The distribution in the hematopoietic cells is shown.

FIG. 12: Posterior and anterior whole body gamma camera images of patient #1, injected 18 hours earlier with 5 mCi $^{131}$I M195 (1.5 mg). All known areas of leukemic involvement (bone marrow, spleen, liver, mediastinal chloroma) show marked uptake of M195.

EXPERIMENT 5

(Lemoli Abstract)
Autologous Bone Marrow Transplantation in Acute Myelogenous Leukemia (AML): In Vitro Treatment with Myeloid-Specific Monoclonal Antibodies (MoAbs) and Drugs in Combination We report the results of a preclinical study comparing four different purging protocols using promyelocytic human cell line HL-60 and myeloid leukemic progenitor cells [CFU-GM-(L)] from AML patients assayed in semisolid culture. We studied the antileukemic effect of 1] complement-dependent lysis by 2 different MoAbs (M195 and F23; 40 ug/ml), reactive with distinct antigens found on early myeloid cells and monocytes, used alone and in combinations; 2] 4-Hydroperoxycyclophosphamide (4-HC) (100 uM/L) alone or 3] combined with VP-16 (5 ug/ml) and 4] a cocktail of 1–3 protocols as above (ie combined immunochemotherapy). Four logs of HL-60 tumor cell elimination was observed after 1 hour incubation with both MoAbs plus 4-HC+VP-16 while the single treatment (ie immunotherapy or chemotherapy) provided 1.5 and 3.0 logs of colony forming inhibition respectively.

When the same protocols were tested on fresh leukemic cells from 4 patients with AML we observed a mean value of CFU-GM-(L) inhibition of 94.7%, 95.5% and 98.6% after MoAbs and complement lysis, 4-HC and 4-HC+VP-16 treatment respectively. The combined treatment of MoAbs and 4-HC+VP-16 produced a 3-log reduction of CFU-GM-(L) colony formation. By comparison the mean recovery of committed normal bone marrow progenitors after incubation with MoAbs and complement was 19.5% for CFU-GM, 32.3% for BFU-E and 16.7% for CFU-MIX. 4-HC+VP-16 treatment showed 4.4% CFU-GM and 5.6% BFU-E recovery. Preliminary data obtained on highly purified CD34+ blast cells, enriched by positive selection, demonstrated the capacity of the immunochemotherapy combined protocol to spare the earliest hematopoietic colony-forming cells. In summary, our results indicate that immunochemotherapy may be a more effective purging strategy for autologous bone marrow transplantation in patients with acute myelogenous leukemia.

EXPERIMENT 6: PREPARATION OF PATIENT FOR REINFUSION (Reference to Experiment 3) (Gulati Protocol)

Patients receiving autologous bone marrow transplantation for the treatment of acute myelogenous leukemia still largely fall due to relapse. This may be due to inadequate preparation of the host or due to inadequate purging. We propose to attempt to improve both aspects of this regimen using cytotxic monoclonal antibodies specific for acute myelogenous leukemia cells and early myeloid progenitors. In htis trial, we will first assess the safety and efficacy of $^{131}$I-M195 to improve on patient conditioning. If this is successful, in a later trial, we will add M195 purging of bone marrow as well. We will not try both at once, at this time, in order that we might assess the effects of each alone.

Phase I toxicity and pharmacology studies with $^{131}$I-M195 done here suggest that in patients with low tumor burden 3–5 rads per mCi will be delivered to the marrow with $^{131}$I-M195. Thus, in the proposed trial here, we expect to deliver specifically to the marrow up to an additional 200, 400 and 600 rads at the three escalating dose levels of 131-M195. Doses to other organs should not be significant.

M195 targets to bone marrow and carries a long range isotope for the preparative regimen such as $^{131}$I or $^{90}$Y instead of the short range isotope such as Bismuth or auger electron generators that are used for killing leukemias as described in Experiment 3 (above) to kill not only the cell on which it is attached but also nearby normal and neoplastic cells. This allows reinfusion of the new marrow. At the same time it kills residual neoplastic cells that may escape the chemotherapy or radiotherapy given as part of the conventional regimen.

This preparative regimen may be (is)? useful for all allogeneic transplants, even those for non-hematopoietic cancer. It may be? is useful in autologous transplants as well.

EXPERIMENT 7: GENETIC RETROVIRAL VECTOR SECTION

Method for Antibody Targeting of Genetic Information into Hematopoietic Cells

Retroviral vectors may be used to introduce exogenous DNA sequences into hematopoietic progenitors and pluripotent stem cells. (Claudio Bordignon, et al, PNAS vol 86:6748–6752 (1989); Stefan Karlsson, et al., PNAS vol 85:6062–6066 (1988); Bruno Goud, Virology vol 163:251–254 (1988); E. Gilboa, Bioessays vol 5(6):252 (1986); W F Anderson, et al, Basic Life Sci. vol 37:59 (1986)) Genetic information encoding, for example, a new gene or part of a gene required for enzyme or hemoglobin function or another required structural protein, is attached to M195 by a retroviral vector. Retroviral vectors usually require receptors for entry into target cells. M195 will substitute for the usual envelope protein involved in this entry and will thus confer specificity for the appropriate cells.

M195 can be attached to the outside of the vector by chemical or genetic means: the M195 could be directly crosslinked to the viral envelope proteins; the M195 could be bound to another antibody or fragment which is directed against the viral envelope proteins; protein A can be inserted genetically into the envelope to bind M195; or M195 can be inserted genetically into the envelope. (see FIG. 13).

REFERENCES (Ref.a)

1. Civin C. I., Mirro J., Banquerigo M. L. MY-1, A New Myeloid-Specific Antigen Identified by a Mouse Monoclonal Antibody. Blood 57:842–845 (1981).
2. Griffen J. D., Ritz J., Nadler L. M., Schlossman S. F. Expression of Myeloid Differentiation Antigens on Normal and Malignant Myeloid Cells. J. Clin. Invest 68:932–941 (1981).
3. Perussia B., Trichieri G., Lebman D., Jankiewicz J., Lange B., Rovera G. Monoclonal Antibodies that Detect Differentiation Surface Antigens on Human Myelomonocytic Cells. Blood 59:382–392 (1982).
4. Andrews R. G., Torok-Storb B., Bernstein I. D. Myeloid-associated Differentiation Antigens on Stem Cells and Their Progeny Identified by Monoclonal Antibodies. Blood 62:124–132 (1983).
5. Griffen J. D., Linch D., Sabbath K., Larcom P., Schlossman S. F. A Monoclnoal Antibody Reactive with Normal and Leukemic Human Myeloid Progenitor Cells. Leuk Res 8:521–534 (1984).
6. Civin C. I., Strauss L. C., Brovall C., Fackler M. J., Schwartz J. F., Shaper J. H. Antigenic Analysis of Hematopoiesis. IIIA Hematopoietic Progenitor Cell Surface Antigen Defined by a Monoclonal Antibody Raised Against KG1a Cells. J Immunol 133L157–165 (1984).
7. Katz F. E., Tindle R., Sutherland D. R., Greaves M. F. Identification of a Membrane Glycoprotein Associated with Hematopoietic Progenitor Cells. Leuk Res 9:191–198 (1985).
8. Askew D. S., Eaves A. C., Takei F. NHL-30.5: A Monoclonal Antibody Reactive with an Acute Myeloid Leukemia (AML)-associated Antigen. Leuk Res 9:135–145 (1985).
9. Ferrero D., Gab bianelli M., Peschle C., Lange B., Rovera G. Surface Phenotypes of Human Hematopoietic Progenitor Cells Defined by Monoclonal Antibodies. Blood 66:946–502 (1985).
10. Drexler H. G., Sagawa K., Menon M., Minowada J. Reactivity Patterns of Myeloid Monoclonal Antibodies with Emphasis on MCS-2. Leuk Res 10:17–23 (1986).
11. Peng R., Al-Katib A., Knowles D. M., Lu L., Borxmeyer H., Tolidjiian B., Chiao J-W, Koziner B., Wang C. Y. Preparation and Characterization of Monoclonal ANtibodies Recognizing Two Distinct Differentiation Antigens (Pro-Im1, Pro-Im2) on Early Hematopoietic Cells. Blood 641169–1178 (1984).
12. Wisniewski D., Knowles R., Wachter M., Strife A., Clarkson B. Expression of Two Natural Killer Cell Antigens, H-25 and H-366, by Human Immature Myeloid Cells and by Erythroid and Granulocytic/Monocytic Colony-Forming Units. Blood 69:419–429 (1987).
13. Strife A., Lambek C., Wisniewski D., Gulati S., Gasson J. C., Golde D. W., Welte K., Gabrilove J. L., Clarkson B. Activities of Four Purified Growth Factors on Highly Enriched Human Hematopoietic Progenitor Cells. Blood 69:1508–1523 (1987).
14. Ball E. D., Mills L. E., Coughlin C. T., Beck R., Cornwell G. G. Autologous Bone Marrow Transplantation in Acute Myelogenous Leukemia: In Vitro Treatment with Myeloid Cell-Specific Monoclonal Antibodies. Blood 68:1311–1315 (1986).
15. Ball E. D., bernier G. M., Cornwell G. G., McIntyre O. R., O'Donnel J. F., Fanger M. W. Monoclonal Antibodies to Myeloid Differentiation Antigens: In Vivo Studies of Three Patients with Acute Myelogenous Leukemia. Blood 62:1203–1210 (1983).
16. Tanimoto M., Scheinberg D. A., Cardo C. C., Huie D., Clarkson B. D., Old L. J. Restricted Expression of an Early Myeloid and Monocytic Cell Surface Antigen Defined by Monoclonal Antibody M195. Leukemia 3:339–348 (1989).
17. Andrews R. G., Takahashi M., Segal G. M., Powell J. S., Bernstein I. D., Singer J. W. The L4F3 Antigen Is Expressed by Unipotent and Multipotent Colony-forming Cells But Not by Their Precursors. Blood 68:1030–1035 (1986).
18. Bernstein I. D., Singer J. W., Andrews R. G., Keating A., Powell J. S., Bjornson B. H., Cuttner J., Najfeld V., Reaman G., Raskind W., Sutton D. M. C., Fialkow P. J. Treatment of Acute Myeloid Leukemia Cells In Vitro with a Monoclonal ANtibody Recognizing a Myeloid Differentiation Antigen Allows Normal Progenitor Cells to be Expressed. J Clin Invest 79:1153–1159 (1987).
19. Bennett J. M., Catovsky D., Daniel M. T., Flandrin G., Galton D. A. G., Gralnick H., Sultan C. Proposed Revised Criteria for the Classification of Acute Myeloid Leukemia. Ann Intern Med 103:626–629 (1985).
20. Peiper S. C., Lemons R. S., Ashmun R. A., Look A. T. DNA-Mediated Transfer of the Gene Encoding p67 (DCD33), a Myeloid Differentiation Antigen Recognized by the MY9, L1B2, and L4F3 Monoclonal Antibodies. In: mcMichael A. J., ed. Leukocyte Typing III. Oxford: Oxford University Press, 622–625 (1986).
21. Alvey P. L., Greaves M. F. A Computer Program for Interpreting Immunophenotypic Data as an Aid to the Diagnosis of Leukemia. Leukemia 1:527–540 (1987).
22. Neame P. B., Soamboonsrup P., Browman G. P., Meyer R. M., Bender A., Wilson W. E. C., Walker I. R, Saeed N., McBride J. A. Classifying Acute Leukemia by Immunophenotyping: a COmbined FAV-Immunologic Classification of AML. Blood 68:1355–1362 (1986).

23. Pessano S., Palumbo A., Ferrero D., Pagliardi G. L., Bottero L., Lai S. K., Meo P., Carter C., Hubbell H., Lange B., Rovera G. Subpopulation Heterogeniety in Human Acute Myeloid Leukemia Determined by Monoclonal Antibodies. Blood 64:275–281 (1984).

24. Griffin J. D., Mayer R. J., Weinstein H. J., Rosenthal D. S., Coral F. S., Bevendga R. P., Schlossman S. f. Surface Marker Analysis of Acute Myeloblastic Leukemia: Identification of Differentiation-Associated Phenotypes. Blood 62:557–563.

25. Van der Reijden H. J., Van Rhenen D. J., Lansdorp P. M., Van't Veer M. D., Langenhuijsen M. M. A. C., Engelfriet C. P., Von dem Borne A. F. G. K. A Comparison of Surface Marker Analysis and FAV Classification in Acute Myeloid Leukemia. Blood 61:443–448 (1983).

26. Linch D. C., Allen C., Beverley P. C. L., Bynoe A. G., Scott C. S., Hogg N. Monoclonal Antibodies Differentiating Between Monocytic and Nonmonocytic Variants of AML. Blood 63:566–573 (1984).

REFERENCES (Ref.b)

1. Foon K. A., Todd R. F. Immunologic Classification of Leukemia and Lymphoma. Blood 68:1–31 (1986).
2. Alvey P. L., Greaves M. F. A Computer Program for Interpreting Immunophenotypic Data as an Aid to the Diagnosis of Leukemia. 1:527–540 (1987).
3. Wilson W. E. C., Walker I. R., Saeed N., McBride J. A. Classifying Acute Leukemia by Immunophenotyping. A COmbined FAB-Immunologic Classification of AML. Blood 68:1355–1362 (1986).
4. Griffin J. D., Linch D., Sabbath F., Larcam P., Schlossman S. F. A Monoclonal Antibody Reactive with Normal and Leukemic Human Myeloid Progenitor Cells. Leuk Res 8:521–534 (1984).
5. Dinndorf P. A., Andrews R. G., Benjamin D., Ridgway D., Wolff L., Bernstein I. D. Expression of Normal Myeloid-Associated ANtigens by Acute Leukemia Cells. Blood 67:1048–1053 (1986).
6. Pessano S. Palumbo A. Ferrero D., Pagliardi G. L., Bottero L., Lai S. k., Meo P., Carter C., Hubbell H., Lange B., Rovera G. Subpopulation Heterogeneity in Human Acute Myeloid Leukemia Determined by Monoclonal Antibodies. Blood 64:275–281 (1984).
7. Griffin J. D., Mayer R. J., Weinstein H. J., Rosenthal D. S., Coral F. S., Bevendga R. P., Schlossman S. F. Surface Marker Analysis of Acute Myeloblastic Leukemia: Identification of Differentiation-Associated Phenotypes. Blood 62:557–563 (1983).
8. Van der Reijden H. J., Van Rhenen D. J., Lansdorp P. M., Van't Veer M. D., Langenhuijsen M. M. A. C., Engelfriet C. P., Von dem Borne A. F. G. K. A Comparison of Surface Marker Analysis and FAV Classification in Acute Myeloid Leukemia. Blood 61:443–448 (1983).
9. Linch D. C., ALlen C., Beverley P. C. L., Bynoe A. G., Scott C. S., Hogg N. Monoclonal Antibodies Differentiation Between Monocytic and Nonmonocytic Variants of AML. Blood 63:566–573 (1984).
10. Drexler H. G., Minowada J. The Use of Monoclonal Antibodies for the Identifcation and Classification of Acute Myeloid Leukemias. Leuk Res 10:279–290 (1986).
11. Ball E. D., Bernier G. M., Cornwell G. G., McIntyre O. R., O'Donnel J. F., Fanger M. W. Monoclonal Antibodies to Myeloid Differentiation Antigens: In Vivo Studies of Three Patients with Acute Myelogenous Leukemia. Blood 62:1203–1210 (1983).
12. Ball E. D., Mills L. E., Coughlin C. T., Beck R., Cornwell G. G. Autologous Bone Marrow Transplantation in Acute Myelogenous Leukemia: In Vitro Treatment with Myeloid Cell-Specific Monoclonal Antibodies. Blood 68:1311–1315 (1986).
13. Griffin J. D., Lowenberg B. Clonogenic Cells in Acute Myeloblastic Leukemia. Blood 68:1185–1195 (1986).
14. Lange B., Ferrero D., Pessano S., Palumbo A., Faust J., Meo P., Rovero G. Surface Phenotype of Clonogenic Cells in Acute Myeloid Leukemia Defined by Monoclonal ANtibodies. Blood 64:693–700 (1984).
15. Sabbath K. D., Ball E. D., Larcom P., Davis R. B., Griffin J. D. Heterogeneity of Clonogenic Cells in Acute Myeloblastic Leukemia. J Clin Invest 75:746–753 (1985).
16. Lowenberg B., Bauman J. G. J. Further Results in Understanding the Subpopulation Structure of AML: Clonogenic Cells and Their Progeny Identified by Differentiation Markers. Blood 66:1225–1232 (1985).
17. Peiper S. C., Lemons R. S., Ashmun R. A., Look A. T. DNA-Mediated Transfer of the Gene Encoding p67 (CD33), a Myeloid Differentiation ANtigen Recognized by the MY9, L1B2, and L4F3 Monoclonal ANtibody. In: McMichael A J, ed. Leucocyte Typing III. New York: Oxford University PRess, 622–625 (1987).
18. Berenson R. J., Bensinger W. I., Kalamasz D. Positive Selection of Viable Cell Populations Using Avidin-Biotin Immunoadsorption. J Immunol Methods 91:11–19 (1986).
19. Katz F. E., Tindle R., Sutherland D. R., Geraves M. F. Identificaiton of a Membrane Glycoprotein Associated with Hematopoietic PRogenitor Cells. Leuk Res 91:191–198 (1985).
20. Civin C. I., Strauss L. C., Brovall C., Fackler M. J., Schwartz J. F., Shaper J. H. Antigenic Analysis of Hematopoiesis. III. A Hematopoietic Progenitor Cell Surface ANtigen Defined by a Monoclonal Antibody Raised Against KG1a Cells. J Immunol 133:157–165 (1984).
21. Strauss L. C., Rowley S. D., LaRussa V. F., Sharkis S. J., Stuart R. K., Civin C. I. Antigenic Analysis of Hematopoiesis. V. Characterization of My-10 Antigen Expression by Normal Lymphohematopoietic Progenitor Cells. Exp Hematol 14:878–886 (1986).
22. Askew D. S., Eaves A. C., Eaves C. J., Takei F. Restricted Expression of a New Acute Myelogenous Leukemia-Associated Antigen (NHL-30.5) on Normal Hemopoietic Progenitor Cells. Blood 67:2098–1102 (1986).
23. Askew D. S., Eaves A. C., Takei F. NHL-30.5: A Monoclonal Antibody Reactive with an Acute Myeloid Leukemia (AML)-Associated Antigen. Leuk Res 9:135–145 (1985).
24. Bernstein J. D., Singer J. W., Andrews R. G., Keeting A., Powell J. S., Bjornson B. H., Cuttner J., Najfeld V., Reaman G., Raskin W., Sutton D. M. C. Fialkow P. J. Treatment of Acute Myeloid Leukemia Cells In Vitro with Monoclonal Antibody Recognizing a Myeloid Differentiation Antigen Allows Normal Progenitor Cells to be Expressed. J Clin Invest 79:1153–1159 (1987).
25. Andrews R. G., Takahashi M., Segal G. M., Powell J. S., Bernstein I. D., Singer J. W., The L4F3 Antigen Is Expressed By Unipotent and Multipotent Colony-forming Cells But Not By Their Precursors, Blood 68:1030–1035 (1986).
26. Andrews R. G., Torok-Storb B., Bernstein I. D., Myeloid-associated Differentiation Antigens on Stem Cells and Their Progeny Identified by Monoclonal Antibodies. Blood 62: 124–132 (1983).

27. Griffin J. D., Ritz J., Nadler L. M., Schlossman S. F., Expression of Myeloid Differentiation Antigens on Normal and Malignant Myeloid Cells. J. Clin. Invest 68:932–941 (1981).
28. Peng R., Al-Katib A., Knowles D. M., Lu L., Broxmeyer H., Tolidjian B., Chiao J-W, Koziner B., Wang C. Y., Preparation and Characterization of Monoclonal Antibodies (Pro-Im1, Pro-Im2) on Early Hematopoietic Cells. Blood 64:1169–1178 (198 ).
29. Wisniewski D., Knowles R., Wachter M., Strife A., Clarkson B., Expression of Two Natural Killer Cell Antigens, H-25 and H-366, By Human Immature Myeloid Cells and By Erythroid and Granulocytic/Monocytic Colony-Forming Units. Blood 69:419–429 (1987).
30. Scheinberg D. A., Tanimoto M., McKenzie S., Strife A., Old L. J., Clarkson B. D., Monoclonal antibody M195: A Diagnostic Marker for Acute Myelogenous Leukemia. Leukemia (1989) (in press).
31. Cairncross J. C., Mattes M. J., Beresford H. R., Albino A. P., Houghton A. N., Lloyd K. O., Old L. J., Cell surface Antigens of Human Astrocytoma Defined by Mouse Monoclonal Antibodies: Identification of Astrocytoma Subsets. Proc. Natl. Acad. Sci. USA 79:5641–5645 (1982).
32. Shiku H. Takahashi T., Oettgen H. F. Old L. J., Cell Surface Antigens of Human Maliganant. II. Serological Typing With Immune Adherence Assays and Definition of Two New Surface Antigens. J Exp Med 144:873–881 (1976).
33. Mattes J. M., Tanimoto M., Pollack M. S., Maurer D. H., Preparing Monolayers of Non-adherent Mammalian Cells. J. Immunol Methods 61:145–150 (1983).
34. Cayre Y., Raynal M. C., Darzykiewicz Z., Dorner M. H., Model For Intermediate Steps in Monocytic Differentiation. Proc. Natl. Acad. Sci. USA 84:7619–7623 (1987).
35. Welt S., Carswell E. A., Vogel C. W., Oettgen H F, Old L. J., Immune and Non-immune Effector Function of IgG3 Mouse Monoclonal Antibody R24 Detecting the Disialoganglioside GD3 On the Surface of Melamoma Cells. Clin Immunol Immunopathol 45:214–229 (1987).
36. Old L. J., Stockert E., Boyse E. A., Kim J. H., Antigenic modulation: Loss of TL Antigen From Cells Exposed to TL Antibody. Study of the Phenomenon In Vitro. J. Exp. Med. 127:523–539 (1968).
37. Berkowitz R. S., Umpierre S. A., Goldstein D. P., Andersen D. J., Cross Reactivity of Monoclonal Antibodies Directed Against Lymphocyte Markers with Trophoblast Cells of Normal Placenta, Hydatidiform Mole, and Gestational Choriocarcinoma. Gynecol Oncol 29:94–100 (1988).
38. Sakamoto J., Furukawa K., Cordon-Cardo C., Yin B. W. T., Rettig W. J., Oettgen H. F., Old L. J., Lloyd K. O. Expression of Lewis (b), X and Y Blood Group Antigens in Human Colonic Tumors and Normal Tissue and in Human Tumor-Derived Cell Lines. Cancer Res. 46:1553–1561 (1986).
39. Drexler H. G., Sagawa K., Menon M., Minowada J., Reactivity Patterns of Myeloid Monoclonal Antibodies with Emphasis On MCS 2, Leukemia Res 10:17–23 (1986).
40. McMichael A. J., ed. Leukocyte Typing III. New York: Oxford University Press, 577–602 (1987).
41. Krolick K. A., Villenmez C., Isakson P., Uhr J. W., Vitetta E. S., Selective Killing of Normal or Neoplastic B Cells by Antibodies Coupled to the A Chain Ricin. Proc. Natl. Acad. Sci. USA 77:5419–5423 (1980).
42. Shimazaki C., Wisniewski D., Scheinberg D. A., Atpodien J., Strife A., Gulati S., Fried J. Wisniewolski R., Wang C. Y., Clarkson B. D., Elimination of Myeloma Cells From Bone Marrow Using Monoclonal Antibodies and Magnetic Immunobeads. Blood 72:1248–1254 (1988).

REFERENCES (Ref.c)

1. Kohler G., Milstein C. Continuous Culture of Fused cells Secreting Antibodis of Pre-defined Specificity. Nature 256:495–497 (1975).
2. Larson S. M. Radiolabeled Monoclonal Anti-tumor Antibodies in Diagnosis and Therapy. J. Nucl. Med 26:538–545 (1985).
3. Houghton A. N., Scheinberg D. A. Monoclonal Antibodies: Potential Applications to the Treatment of Cancer. Sem Oncol 13:165–179 (1986).
Goldenberg D. M., Deland F., Kim E. et al. Use of Radiolabeled Antibodies to Carcinoembryonic Antigen for the Detection and Localization of Diverse Cancers by External Photoscanning. N. Engl. J. Med. 298:1384–1388 (1978).
5. Bunn P. A., Jr., Carrasquillo J. A., Keenan A. M. et al. Imaging of T-cell Lymphoma by Radiolabeled Monoclonal Antibody. Lancet 2:1219–1221 (1984).
Larson S. M., Brown J. P., Wright P. W. et al. Imaging of Melanoma With 1-131 Labeled Monoclonal Antibody. J. Nucl. Med 24:123–129 (1983).
7. Press O. W., Eary J. F., Badger C. C. et al. Treatment of Refractory Non-hodgkin's Lymphoma With Radiolabeled MB-1 (Anti-CD37) Antibody. J. Clin. Oncol 7:1027–1038 (1989).
8. Rosen S., Zimmer A., Golman-Leikin R. et al. Radioimmunodetection and Radioimmunotherapy of Cutaneous T-cell Lymphomas Using an $^{131}$I-labeled Monoclonal Antibody. J. Clin. Oncol. 5:562–573 (1987).
9. Carrasquillo J. A., Bunn P. A., Keenan A. A. et al. Radioimmunodetection of Cutaneous T-cell lymphoma with $^{111}$In-labeled T101 Monoclonal Antibody. N. Engl. J. Med. 315:673–680 (1986).
10. Eptein A. L., Zimmer A. M., Spies S. M. et al. Radioimmunodetection of Human B-cell Lymphomas With a Radiolabeled Tumor-specific Monoclonal Antibody (Lym-1). In Maliganant Lymphomas and Hodgkin's Disease: Experimental and Therapeutic advances, Cavalli F., Bonadonna G., Rozencweig M., eds Boston Martinus Nijhoff (1985)
11. DeNardo S. J., DeNardo G. L., O'Grady L. F. et al. Pilot Studies of Radioimmunotherapy of B Cell Lymphoma and Leukemia Using I-131 Lym-1 monoclonal Antibody. Antibody Immunoconj Radiopharm 1:17–33 (1988).
12. Rao D. V., Narra V. R., Howell R. W. et al. In-vivo Radiotoxicity of DNA-incorporated $^{125}$I Compared With That of Densely Ionizing Alpha-particles. Lancet vol.2:650–653 (Sep. 16, 1989).
13. Woo D. V., Li D., Mattis J. A. et al. Cancer Res. 49:2952–2952 (1989).
14. Scheinberg D. A., Strand M. Kinetic and Catabolic Considerations of Monoclonal Antibody Targeting in Erythroleukemic Mice. Cancer Res. 43:265–272 (1983).
15. Khaw B. A., Cooney J., Edgington T., et al. Differences in Experimental Tumor Localization of a Dual-labeled Monoclonal Antibody. J. Nucl. Med. 27:1293–1299 (1986).
16. Carrasquillo J. A., Mulshine J. L., Bunn P. A., Jr. et al. Indium-111 T101 Monoclonal Antibody is Superior to Iodine-131 T101 in Imaging of Cutaneous T-cell Lymphoma. J. Nucl. Med. 28:281–287 (1987).

17. Anderson W. M., Strand M., Radiolabeled Antibody: Iodine Versus Radiometal Chelates. NCI Monogr 3:149–151.

18. Lamm M. E., Boyse E. A., Old L. J. et al. Modulation of TL (thymus-leukemia) Antigens by Fab-fragments of TL Antibody. J. Immunol. 101:99–103 (1968)

19. Shawler D. L., Micelli M. C., Wormsley S. B., Royston L, Dillman R. O. Induction of In Vitro and In Vivo Antigenic Modulation by the Anti-human T-cell Monoclonal Antibody T101. Cancer Res. 44:5921–5927 (1984).

20. Press O. W., Farr A. G., Borroz K. I. et al. Endocytosis and Degradation of Monoclonal Antibodies Trargeting Human B-cell Malignancies. Cancer Res. 49:4906–49012 (1989).

21. Matzku S., Brocker E.-B., Brugen J. et al. Modes of Binding and Internalization of Monoclonal Antibodies to Human Melanoma Cells Lines. Cancer Res. 46:3848–3854 (1986).

22. Wang B. So, Lumanglas A. L., Silva J. et al. Internalization and Re-expression of Antigens of Human Melanoma Cells Following Exposure to Monoclonal Antibody. Cell Immunol. 106:12–21 (1987).

23. Olsnes S., Sandvig K., Petersen O. W., van Deurs B. Immunotoxins—Entry Into Cells and Mechanisms of Action. Immunol. Today 10:290–295 (1989).

24. Tanimoto M., Scheinberg D. A., Cordon-Cardo C., Huie D., Clarkson B. D., Old L. J., Restricted Expression of an Early Myeloid and Monocytic Cell Surface Antigen Defined by Monoclonal Antibody M195. Leukemia 3:339–348 (1989).

25. Scheinberg D. A., Tanimoto M., McKenzie S., Strife A., Old L. J., Clarkson B. D., Monoclonal Antibody M195: A diagnostic Marker for Acute Myelogenous Leukemia. Leukemia 3:440–445 (1989).

26. Mittler R. S., Talle M. A., Carpender K. et al. Generation and Characterization of Monoclonal Antibodies Reactive With Human B Lymphocytes. J. Immuno 131:1754–1761 (1983).

27. Nemerow G. R., Wolfert R., McNaughton M. E. et al. Identification and Characterization of the Epstein-Barr Virus Receptor on Human B Lymphocytes and Its Relationship to the C3d Complement Receptor (CR2). J. Virol. 55:347–351 (1985).

28. Hunter W. M., Greenwood F. C., Preparation of Iodine-131 Labelled Human Growth Hormone of High Specificity Activity. Nature 194:495–496 (1962).

29. Lindmo T., Boven E., Cuttitta F. et al. Determination of Immunoreactive Fraction of Radiolabeled Monoclonal Antibody By Linear Extrapolation to Binding at Infinite Antigen Excess. J. Immunol Methods 72:77–89 (1984).

30. Badger C. C., Krohn K. A., Bernstein I. D. In Vitro Measurement Of Avidity of Radioiodinated Antibodies. Nucl. Med. Biol. 14:605–610 (1987).

Krejcarek G. E., Tucker K. L. Covalent Attachment of Chelating Groups to Macromolecules. Biochem. Biophy. Res. Commun 77:581–585 (1977)

32. The Gansow Paper in Cancer Res. 89.

What is claimed is:

1. A therapeutic agent comprising humanized monoclonal antibody M195 (ATCC HB 10306) and a cytotoxic agent conjugated thereto, wherein the cytotoxic agent is a polypeptide toxin.

2. A therapeutic agent comprising humanized monoclonal antibody M195 (ATCC HB 10306) and a cytotoxic agent conjugated thereto, wherein the cytotoxic agent is an alpha particle emitter.

3. The therapeutic agent of claim 2, wherein the alpha particle emitter is selected from the group consisting of Lead-212, Bismuth-212, and Astatine-212.

4. The therapeutic agent of claim 3, wherein the alpha particle is Bismuth-212.

5. The therapeutic agent of claim 3, wherein the alpha particle emitter is conjugated to the monoclonal antibody by means of a bifunctional chelate.

6. A therapeutic agent comprising humanized monoclonal antibody M195 (ATCC HB 10306) and a cytotoxic agent conjugated thereto, wherein the cytotoxic agent is a beta particle emitter selected from the group consisting of Scandium-47, Rhenium-186, Rhenium-188, and Yttrium-90.

7. The therapeutic agent of claim 6, wherein the beta particle emitter is Scandium-47.

8. The therapeutic agent of claim 6, wherein the beta particle emitter is Yttrium-90.

9. A therapeutic agent comprising humanized monoclonal antibody M195 (ATCC HB 10306) and a cytotoxic agent conjugated thereto, wherein the cytotoxic agent is an auger electron generator selected from the group consisting of Iodine-123, Bromine-77, and Indium-111.

10. The therapeutic agent of claim 9, wherein the auger electron generator is Iodine-123.

11. A therapeutic agent comprising humanized monoclonal antibody M195 (ATCC HB 10306) and a cytotoxic agent conjugated thereto, wherein the cytotoxic agent is a fissionable nuclide selected from the group consisting of Boron-10 and an Actinide.

12. A method of treating acute or chronic myeloid leukemia in a human patient which comprises administering to the patient an amount of a therapeutic agent comprising humanized monoclonal antibody M195 (ATCC HB 10306) and a cytotoxic agent conjugated thereto sufficient to bind to, and be internalized by, leukemic cells which express the antigen to which M195 binds so as to thereby destroy the leukemic cells.

13. The method of claim 12, wherein the amount of therapeutic agent is from about 0.05 mg. to about 100 mg.

14. The method of claim 12, wherein the therapeutic agent is administered intravenously.

15. The method of claim 12, wherein the cytotoxic agent is Iodine-131 and Iodine-121 comprises an amount from about 50 mCi to about 200 mCi.

16. The method of claim 12, wherein the cytotoxic agent is Yttrium-90 and Yttrium-90 comprises an amount from about 10 mCi to about 50 mCi.

17. The method of claim 12, wherein the cytotoxic agent is Bismuth-212 and Bismuth-212 comprises an amount from about 20 mCi to about 80 mCi.

18. The method of claim 12, wherein the cytotoxic agent is Iodine-123 and Iodine-123 comprises an amount from about 100 mCi to about 300 mCi.

19. A method of destroying a human myeloid leukemia patient's bone marrow cells which comprises administering to the patient a therapeutic agent comprising humanized monoclonal antibody M195 (ATCC HB 10306) and a cytotoxic agent conjugated thereto under conditions such that the therapeutic agent binds to, and is internalized by, bone marrow cells which express the M195 antigen in an amount sufficient to destroy the patient's bone marrow cells.

20. The method of claim 19, wherein the amount of antibody is from about 0.01 mg to about 50 mg.

21. The method of claim 19, wherein the therapeutic agent is administered intravenously.

* * * * *